United States Patent [19]

Meki

[11] Patent Number: 5,036,158
[45] Date of Patent: Jul. 30, 1991

[54] INTERMEDIATE COMPOUNDS FOR AN INSECTICIDAL AND ACARICIDAL PYRAZOLE COMPOUND

[75] Inventor: Naoto Meki, Kobe, Japan

[73] Assignee: Sumitomo Chemical Company, Limited, Osaka, Japan

[21] Appl. No.: 609,622

[22] Filed: Nov. 6, 1990

Related U.S. Application Data

[63] Continuation-in-part of Ser. No. 569,223, Aug. 17, 1990, which is a continuation of Ser. No. 496,176, Mar. 20, 1990, abandoned, which is a continuation of Ser. No. 348,217, May 5, 1989, abandoned.

[30] Foreign Application Priority Data

| May 6, 1988 | [JP] | Japan | 63-111046 |
|---|---|---|---|
| Jul. 15, 1988 | [JP] | Japan | 63-177749 |
| Jan. 20, 1989 | [JP] | Japan | 1-12672 |
| Feb. 27, 1989 | [JP] | Japan | 1-47344 |

[51] Int. Cl.$^5$ .................................. C07D 239/20
[52] U.S. Cl. .................................. 564/300; 564/301
[58] Field of Search .................................. 564/300, 301

[56] References Cited

U.S. PATENT DOCUMENTS 4,751,245 6/1988 Bisacchi et al. .................. 564/300

OTHER PUBLICATIONS

European Patent Application, 341,048, 11-8-89.

*Primary Examiner*—Robert W. Ramsuer
*Attorney, Agent, or Firm*—Stevens, Davis, Miller & Mosher

[57] ABSTRACT

There are disclosed intermediate compounds of the formula,

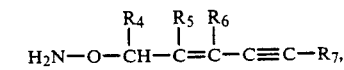

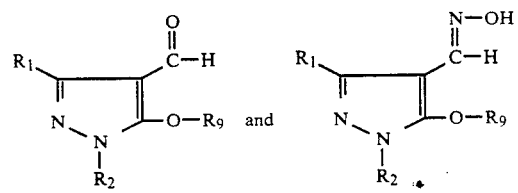

wherein the substitutents of $R_1$ to $R_7$ and $R_9$ have the same meanings as described in the text, for producing a insecticidal and acaricidal pyrazole compound represented by the formula,

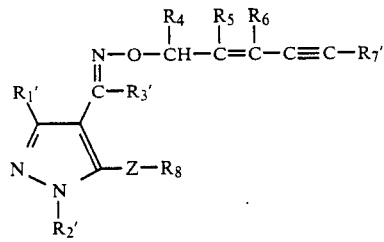

wherein the substitutents of $R_1'$ to $R_8$ and the symbol Z have the specified meanings as described in the text.

5 Claims, No Drawings

INTERMEDIATE COMPOUNDS FOR AN INSECTICIDAL AND ACARICIDAL PYRAZOLE COMPOUND

CROSS-REFERENCE TO RELATED APPLICATIONS:

This is a continuation-in-part of application Ser. No. 07/569,223, filed on Aug. 17, 1990 which is a continuation application of Ser. No. 07/496,176 filed on Mar. 20, 1990, now abandoned which is in turn a continuation application of Ser. No. 07/348,217 filed on May 5, 1989, now abandoned.

The present invention relates to intermediate compounds for an insecticidal and acaricidal pyrazole compound.

That a certain kind of pyrazole compounds has an insecticidal and acaricidal activity is disclosed in EP 234045A2 and JP-A-64-13086.

These compounds, however, may not always be said to be satisfactory in terms of the efficacy and spectrum.

In view of this situation, the present inventors have extensively studied to develop a compound having excellent activity, and as a result, have found that the pyrazole compound represented by the following formula (I) has particularly excellent insecticidal activity and has acaricidal activity, and that intermediate compounds represented by the formula (II), (IV) and (V) are useful for producing them. The present inventors thus completed the present invention.

The present invention provides intermediates for producing the pyrazole compound represented by the formula (I):

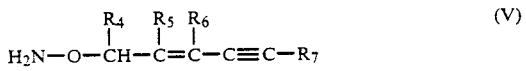
(V)

wherein each of $R_4$, $R_5$ and $R_6$, which may be the same or different, is a hydrogen atom or a $C_1$-$C_3$ alkyl group, or optional two of them may be bonded together to form a $C_2$-$C_4$ alkylene chain; and $R_7$ is a hydrogen atom, a $C_1$-$C_8$ alkyl group; a $C_1$-$C_8$ chloro- or fluoro-alkyl group; a $C_2$-$C_8$ alkoxyalkyl group; or a $C_3$-$C_8$ cycloaklyl or phenyl group which may be substituted with a $C_1$-$C_3$ alkyl, $C_1$-$C_3$ alkoxy group, or a chlorine or fluorine atom;

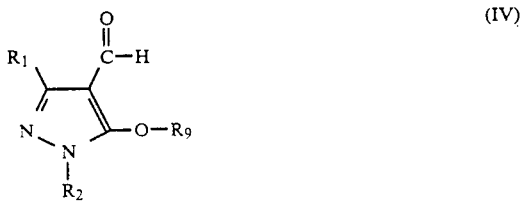
(IV)

wherein $R_1$ is a hydrogen atom, or a $C_1$-$C_3$ alkyl group; $R_2$ is a $C_1$-$C_3$ alkyl group or a $C_1$-$C_3$ chloro-, bromo- or fluoro-alkyl group; $R_9$ is a $C_3$-$C_8$ alkyl, $C_2$-$C_8$ chloro-, bromo- or fluoro-alkyl, $C_3$-$C_8$ alkenyl, $C_3$-$C_8$ chloro-, bromo- or fluoro-alkenyl, $C_3$-$C_8$ alkynyl, $C_2$-$C_{10}$ alkoxyalkyl, $C_2$-$C_{10}$ alkylthioalkyl group; a $C_3$-$C_8$ cycloalkyl group which may be substituted with a $C_1$-$C_3$ alkyl, $C_1$-$C_3$ alkoxy group, or chlorine, bromine or fluorine atom, or a group represented by

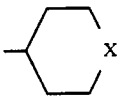

(in which X is an oxygen or sulfur atom); and

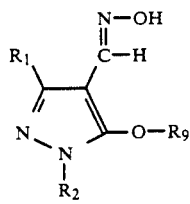
(II)

wherein $R_1$ is a hydrogen atom, or a $C_1$-$C_3$ alkyl group; $R_2$ is a $C_1$-$C_3$ alkyl group or a $C_1$-$C_3$ chloro-, bromo- or fluoro-alkyl group; $R_9$ is a $C_3$-$C_8$ alkyl, $C_2$-$C_8$ chloro-, bromo- or fluoro-alkyl, $C_3$-$C_8$ alkenyl, $C_3$-$C_8$ chloro-, bromo- or fluoro-alkenyl, $C_3$-$C_8$ alkynyl, $C_2$-$C_{10}$ alkoxyalkyl, $C_2$-$C_{10}$ alkylthioalkyl group; a $C_3$-$C_8$ cycloalkyl group which may be substituted with a $C_1$-$C_3$ alkyl, $C_1$-$C_3$ alkoxy group, or chlorine, bromine or fluorine atom, or a group represented by

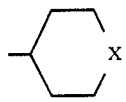

(in which X is an oxygen or sulfur atom).

In view of the insecticidal and/or araricidal activity of the compounds (I) derived from the compound (V), (IV) or (II), the following preferred compound will be mentioned:

The compound (V) wherein $R_4$, $R_5$ and $R_6$, which may be the same or different is a hydrogen atom or a methyl group is preferred.

The compound (V) wherein $R_4$, $R_5$ and $R_6$ is a hydrogen atom is more preferred.

The compound (V) wherein $R_4$, $R_5$ and $R_6$ is a hydrogen atom, and $R_7$ is a hydrogen atom; a $C_1$-$C_8$ alkyl group; a $C_1$-$C_8$ chloro- or fluoro-alkyl group; a $C_2$-$C_8$ alkoxyalkyl group; or a $C_3$-$C_8$ cycloalkyl group which may be substituted with a $C_1$-$C_3$ alkyl, $C_1$-$C_3$ alkoxy group, or a chlorine or fluorine atom is particularly preferred.

The compound (V) wherein $R_4$, $R_5$ and $R_6$ is a hydrogen atom, and $R_7$ is a hydrogen atom; a $C_1$-$C_8$ alkyl group; a $C_2$-$C_8$ alkoxyalkyl group; or a $C_3$-$C_8$ cycloalkyl groups which may be substituted with a $C_1$-$C_3$ alkyl, $C_1$-$C_3$ alkoxy group, or a chlorine or fluorine atom is most preferred.

The compound (IV) or (II) wherein $R_2$ is a methyl group is preferred.

The compound (IV) or (II) wherein $R_2$ is a methyl group; $R_9$ is a $C_3$-$C_8$ alkyl, $C_2$-$C_8$ chloro-, bromo- or fluoro-alkyl, $C_2$-$C_{10}$ alkoxyalkyl, $C_2$-$C_{10}$ alkylthioalkyl group; a cycloalkyl group which may be substituted with a $C_1$-$C_3$ alkyl, $C_1$-$C_3$ alkoxy group, or chlorine, 1 bromine or fluorine atom; or a group represented by

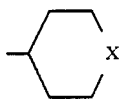

(in which X is an oxygen or sulfur atom) is more preferred.

The compound (IV) or (II) wherein $R_1$ is a methyl group; $R_2$ is a methyl group; $R_9$ is a $C_3$-$C_8$ alkyl, $C_2$-$C_8$ chloro-, bromo- or fluoro-alkyl, $C_2$-$C_{10}$ alkoxyalkyl, $C_2$-$C_{10}$ alkylthioalkyl group which may be substituted with a $C_1$-$C_3$ alkyl, $C_1$-$C_3$ alkoxy group, or chlorine, bromine or fluorine atom; or a group represented by

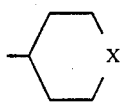

(in which X is an oxygen or sulfur atom) is particularly preferred.

The compound (IV) or (II) wherein $R_1$ is a methyl group; $R_2$ is a methyl group; $R_9$ is an $C_3$-$C_8$ alkyl, $C_2$-$C_8$ chloro-, bromo- or fluoro-alkyl group or a $C_3$-$C_8$ cycloalkyl group which may be substituted with a $C_1$-$C_3$ alkyl, $C_1$-$C_3$ alkoxy group, or chlorine, bromine or fluorine atom is most preferred.

Some of the pyrazole compound having the formula (I) which may be produced by using the intermediates of the present invention is:

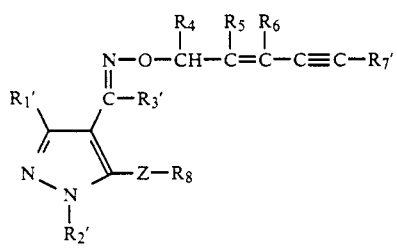

wherein $R_1'$ is a hydrogen atom, or an alkyl or phenyl group; $R_2'$ is a hydrogen atom, or an alkyl or haloalkyl group; $R_3'$ is a hydrogen atom, or an alkyl or phenyl group; each of $R_4$, $R_5$ and $R_6$, which may be the same or different, is a hydrogen atom or an alkyl group, or optional two of them may be bonded together to form an alkylene chain; $R_7'$ is a hydrogen atom, an alkyl group, haloalkyl group, alkenyl group, alkoxyalkyl group, or a cycloalkyl, cycloalkenyl, phenyl or pyridyl group which may be substituted; $R_8$ is an alkyl, haloalkyl, alkenyl, haloalkenyl, alkynyl, alkoxyalkyl, alkylthioalkyl or mono- or dialkylaminoalkyl group, a cycloalkyl group which may be substituted, a group represented by

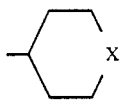

(in which X is an oxygen or sulfur atom), or a group represented by

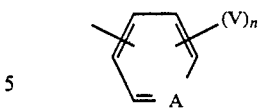

(in which each of V's, which may be the same or different, is a hydrogen or halogen atom, or an alkyl, haloalkyl, alkoxyl, haloalkoxyl or methylenedioxy group, A is a nitrogen atom or a methine group, and n is an integer of from 1 to 5); and Z is an oxygen or sulfur atom.

The formula (I) representing the present compounds will be explained. In $R_1'$, the alkyl group is a $C_1$-$C_3$ alkyl group. In $R_2'$, the alkyl and haloalkyl groups are a $C_1$-$C_3$ alkyl group and the same group substituted with chlorine, bromine or fluorine, respectively. In $R_3'$, the alkyl group is a $C_1$-$C_2$ alkyl group. In $R_4$, $R_5$ and $R_6$, the alkyl group is a $C_1$-$C_3$ alkyl group, and the alkylene chain is a $C_2$-$C_4$ alkylene chain. In $R_7'$, the alkyl, haloalkyl, alkenyl, alkoxyalkyl, cycloalkyl, and cycloalkenyl groups are a $C_1$-$C_8$ alkyl group, a $C_1$-$C_8$ alkyl group substituted with a chlorine, bromine, or fluorine atom, a $C_2$-$C_8$ alkenyl group, a $C_2$-$C_8$ alkoxyalkyl group, a $C$-$C$ cycloalkyl group and a $C_3$-$C_8$ cycloalkenyl group, respectively and the substituents of the cycloalkyl, cycloalkenyl, phenyl and pyridyl groups include a $C_1$-$C_3$ alkyl group, a $C_1$-$C_3$ alkoxyl group and a halogen atom (e.g. chlorine, bromine, fluorine). In $R_8$, the alkyl, alkenyl and alkynyl groups are those having 1(2) to 8 carbon atoms; the haloalkyl and haloalkenyl groups are those having 1(2) to 8 carbon atoms substituted with a chlorine, bromine or fluorine atom; the alkoxyalkyl, alkylthioalkyl and mono- or dialkylaminoalkyl groups are those having 2 to 10 carbon atoms; the cycloalkyl group is a $C_3$-$C_8$ cycloalkyl group; and the substituent of the cycloalkyl group includes a $C_1$-$C_3$ alkyl group, a $C_1$-$C_3$ alkoxyl group and a halogen atom (e.g. chlorine, bromine, fluorine). In V, the halogen atom is a chlorine, bromine or fluorine atom; the alkyl group is a $C_1$-$C_3$ alkyl group; the haloalkyl group is a $C_1$-$C_2$ alkyl group substituted with a chlorine, bromine or fluorine atom; the alkoxyl group is a $C_1$-$C_2$ alkoxyl group; and the haloalkoxyl group is a $C_1$-$C_2$ alkoxyl group substituted with a chlorine, bromine or fluorine atom.

Preferred compounds which may be produced from the intermediates of the present invention, include those represented by the formula (I) in which $R_1'$ is a hydrogen atom or an alkyl group, $R_2'$ is a methyl group, $R_3'$ is a hydrogen atom, and Z is an oxygen atom. More preferred ones are those represented by the formula (I) in which all of $R_4$, $R_5$ and $R_6$ are hydrogen atoms and $R_1'$, $R_2'$ and $R_3'$ have the same meanings as mentioned above. Illustrative examples, include the following.

1,3-Dimethyl-5-cyclopentyloxypyrazol-4-carboaldoxime O-6,6-dimethylhept-2-ene-4-ynyl ether 1,3-Dimethyl-5-cyclohexyloxypyrazol-4-carboaldoxime O-6,6-dimethylhept-2-ene-4-ynyl ether 1,3-Dimethyl-5-isopropyloxypyrazol-4-carboaldoxime O-6,6-dimethylhept-2-ene-4-ynyl ether 1,3-Dimethyl-5-n-butyloxypyrazol-4-carboaldoxime O-6,6-dimethylhept-2-ene-4-ynyl ether 1,3-Dimethyl-5-(3-methylbutyloxy)pyrazol-4carboaldoxime O-6,6-dimethylhept-2-ene-4-ynyl ether 1,3-Dimethyl-5-phenoxypyrazol-4-carboaldoxime O-6,6-dimethylhept-2-ene-4-ynyl ether 1,3-Dimethyl-5-(p-fluorophenoxy)pyrazol-4carboaldoxime O-6,6-dimethylhept-2-ene-4-ynyl ether 1,3-Dimethyl-5-(p-chlorophenoxy)pyrazol-4carboaldoxime O-6,6-dimethylhept-2-ene-4-ynyl ether 1,3-Dimethyl-5-(m-fluorophenoxy)pyrazol-4carboaldoxime O-6,6-dimethylhept-2-ene-4-ynyl ether 5   1,3-Dimethyl-5-phenoxypyrazol-4-carboaldoxime O-5-cyclohexylpent-2-ene-4-ynyl ether 1,3-Dimethyl-5-(p-fluorophenoxy)pyrazol-4carboaldoxime O-5-cyclohexylpent-2-ene-4-ynyl ether 1,3-Dimethyl-5-(p-methyloxyphenoxy)pyrazol-4carboaldoxime O-6,6-dimethylhept-2-ene-4-ynyl ether 1,3-Dimethyl-5-(p-methylphenoxy)pyrazol-4carboaldoxyme O-6,6-dimethylhept-2-ene-4-ynyl ether.

Insect pests against which the present compounds are effective include Hemiptera such as planthoppers, leafhoppers, aphids, bugs, whiteflies, etc.; Lepidoptera such as diamond-back moth (*Plutella xylostella*), rice stem borer (*Chilo suppressalis*), rice leafroller (*Cnaphalocrocis medinalis*), armyworms and cutworms, Plusiid moths (*Plusiinae*), small white butterfly (*Pieris rapae crucivora*), casemaking clothes moth (*Tinea pellionella*), webbing clothes moth (*Tineola bisselliella*), etc.; Diptera such as common mosquito (*Culex pipiens pallens*), Anopheline mosquito (*Anopheles spp.*), Aedes mosquito (*Aedes spp.*), housefly (*Musca domestica*), etc.; Dictyoptera such as German cockroach (*Blattella germanica*), smokybrown cockroach (*Periplaneta fuliginosa*), brown cockroach (*Periplaneta brunnea*), American cockroach (*Periplaneta americana*), etc.; Coleoptera, Hymenoptera, Thysanoptera, Orthoptera, etc.; and spider mites such as carmine spider mite (*Tetranychus cinnabarinus*), twospotted spider mite (*Tetranychus urticae*), citrus red mite (*Panonychus citri*), etc. Further, the compounds represented by formula (I) are also effective against insect pests having an increased resistance to the existing insecticides and acaricides.

The following compound, which is closely related with the claimed compound, is described in Khim.-Farm. Zh., 4(3), 19–24 [Chemical Abstracts, Vol. 73, 330, (1970), 3844w]

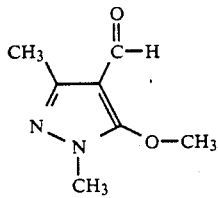
(C)

The claimed compound as the intermediate from which some of the insecticidal and acaricidal compound (I) described in EP-341,048-A1 can be produced is also used as a substitute for the intermediate of the compounds, having the insecticidal, acaricidal and fungicidal activities, described in EP-234,045-A2.

Some of the compounds (I) can be produced, for example, by the following methods.

Method A:

A method of obtaining some of the compounds (I) by reacting a compound represented by the formula (II),

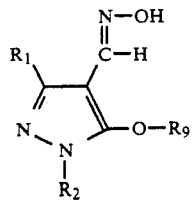
(II)

wherein $R_1$, $R_2$ and $R_9$ are the same as defined above, with a compound represented by the formula (III),

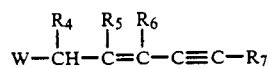
(III)

wherein $R_4$, $R_5$, $R_6$ and $R_7$ are the same as defined above, and W is a halogen atom.

Method B:

A method of obtaining some of the compounds (I) by reacting a compound represented by the formula (IV),

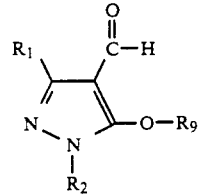
(IV)

wherein $R_1$, $R_2$ and $R_9$ are the same as defined above, with a compound represented by the formula (V),

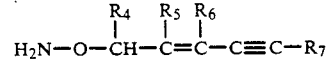
(V)

wherein $R_4$, $R_5$, $R_6$ and $R_7$ are the same as defined above.

In Method A, a solvent is not always necessary for the reaction, but when a solvent is used, the following are examples thereof: Ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), sulfolane dimethyl sulfoxide, aromatic hydrocarbons (e.g. benzene, toluene, chlorobenzene), halogenated hydrocarbons (e.g. methylene chloride, chloroform), ketones (e.g. acetone, methyl isobutyl ketone), nitriles (e.g. acetonitrile), pyridines (e.g. pyridine, picoline), water and mixtures of these solvents. The compound of the formula (III) is used in an amount of from 0.5 to 10 moles based on 1 mole of the compound of the formula (II). The reaction temperature is usually from −20° to 200° C., preferably from −10° to 100° C. The reaction time is usually from 5 minutes to 100 hours, preferably from 30 minutes to 50 hours.

Usually, in carrying out this reaction, the following compounds are used as an acid-binding agent: Alkali metal hydroxides (e.g. lithium hydroxide, sodium hydroxide, potassium hydroxide), alkali metal carbonates (e.g. sodium carbonate, potassium carbonate), alkali metal hydrides (e.g. lithium hydride, sodium hydride, potassium hydride), alkali metals (e.g. metallic lithium, metallic sodium, metallic potassium), alkali metal alkoxides (e.g. sodium methoxide, sodium ethoxide) and mixtures thereof. The amount of the acid-binding agent used is from 0.5 to 10 moles based on 1 mole of the compound of the formula (II). If necessary, a phase transfer catalyst such as ammonium salts (e.g. tetra-n-butylammonium bromide, benzyltrimethylammonium chloride), ethers (e.g. 18-Crown-6), amines [e.g. tris(3,6-dioxoheptyl)amine (TDA-1)], etc. may be used in an amount of from 0.0001 to 1 mole based on 1 mole of the compound of the formula (II).

After completion of the reaction, the present compounds can be obtained by the usual after-treatments.

In Method B, a solvent is not always necessary for the reaction, but when a solvent is used, the following are examples thereof: Ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), sulfolane, dimethyl sulfoxide, aromatic hydrocarbons (e.g. benzene, toluene, chlorobenzene), halogenated hydrocarbons (e.g. methylene chloride, chloroform), aliphatic hydrocarbons (e.g. pentane, hexane, heptane, cyclohexane), pyridines (e.g. pyridine, picoline), acetic acid, water and mixtures of these solvents. The compound of the formula (V) is used in an amount of from 0.5 to 10 moles based on 1 mole of the compound of the formula (IV). The reaction temperature is usually from $-20°$ to $200°$ C., preferably from $-10°$ to $150°$ C. The reaction time is usually from 5 minutes to 100 hours, preferably from 5 minutes to 20 hours. If necessary, the following may be used as a catalyst for the reaction: Mineral acids (e.g. hydrochloric acid, sulfuric acid, nitric acid), organic acids (e.g. formic acid, acetic acid, propionic acid, methanesulfonic acid, benzenesulfonic acid, p-toluenesulfonic acid), amine/acid adducts (e.g. pyridine hydrochloride, triethylamine hydrochloride, morpholine hydrochloride), etc. The amount of the catalyst used is from 0.001 to 1 mole based on 1 mole of the compound of the formula (IV).

After the completion of the reaction, the present compounds can be obtained by the usual after- c treatments.

The compound represented by the formula (III) can be obtained, for example, by reacting a compound represented by the formula (VIII),

wherein $R_4$, $R_5$ and $R_6$ are the same as defined above, with a compound represented by the formula (IX),

wherein $R_7$ is the same as defined above, to obtain a compound represented by the formula (X),

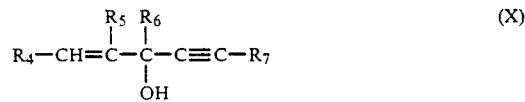

wherein $R_4$, $R_5$, $R_6$ and $R_7$ are the same as defined above, and then subjecting the resulting compound (X) to rearrangement and halogenation.

In carrying out the first reaction, a solvent is usually used. The solvent used includes ethers (e.g. diethyl ether, diisopropyl ether, tetrahydrofuran, dioxane), aromatic hydrocarbons (e.g. benzene, toluene), alcohols (e.g. ethylene glycol, glycerin, methanol, ethanol), amides (e.g. N,N-dimethylformamide), sulfoxides (e.g. dimethyl sulfoxide, sulfolane), water and mixtures thereof. In this reaction, a base is usually used. The base used includes alkyllithiums (e.g. n-butyllithium), phenyllithiums, alkylmagnesium halides (e.g. ethylmagnesium bromide), alkali metal hydrides (e.g. lithium hydride, sodium hydride, potassium hydride), alkali metal hydroxides (e.g. lithium hydroxide, sodium hydroxide, potassium hydroxide), alkali metals (e.g. lithium, sodium, potassium), etc.

As to the amounts of the reagents used for the reaction, the amount of the compound of the formula (IX) is from 0.1 to 10 moles, preferably from 0.5 to 2 moles based on 1 mole of the compound of the formula (VIII), and that of the base is from 0.5 to 2 moles based on the same. The reaction temperature is usually from $-100°$ to $300°$ C., and the reaction time is usually from 5 minutes to 100 hours, preferably from 30 minutes to 50 hours. As an auxiliary for the reaction, a phase transfer catalyst such as ammonium salts (e.g. tetra-n-butylammonium bromide, benzyltrimethylammonium chloride), ethers (e.g. 18-Crown-6), tris(3,6-dioxoheptyl)amine (TDA-1), etc. may be used in an amount of from 0.0001 to 1 mole based on 1 mole of the compound of the formula (VIII).

After the completion of the reaction, the compound of the formula (X) can be obtained by the usual after-treatments.

In the second reaction to produce the compound of the formula (III) by the rearrangement and halogenation of the compound of the formula (X), a solvent may not always be used. However, when a solvent is used, a solvent such as halogenated hydrocarbons (e.g. methylene chloride, chloroform, dichloroethane), hydrocarbons (e.g. hexane, heptane, aromatic hydrocarbons (e.g. benzene, toluene, chlorobenzene), alcohols (e.g. methanol, ethanol, isopropanol), water and mixtures thereof may usually be used. As the halogenating agent used in reaction, usual ones such as thionyl chloride, phosphorus tribromide, hydrochloric acid, hydrobromic acid, hydroiodic acid, etc. may be used.

As to the amount of the reagent used for the reaction, the amount of the halogenating agent is from 0.1 to 10 moles, preferably from 0.5 to 3 moles based on 1 mole of the compound of the formula (X). The reaction temperature is usually from $-30°$ to $200°$ C., preferably from $-20°$ to $150°$ C. The reaction time is usually from 5 minutes to 100 hours, preferably from 30 minutes to 50 hours. As an auxiliary for the reaction, compounds such as amides (e.g. N,N-dimethylformamide), pyridines (e.g. pyridine, picoline), anilines (e.g. N,N-dimethylaniline), aliphatic amines (e.g. triethylamine), etc. may be used in an amount of from 0.0001 to 1 mole based on 1 mole of the compound of the formula (X).

After the completion of the reaction, the compound of the formula (III) can be obtained by the usual after-treatments.

The compound represented by the formula (V) can be obtained by reacting the compound represented by the formula (III) with a compound represented by the formula (XI),

wherein Y is a group represented by

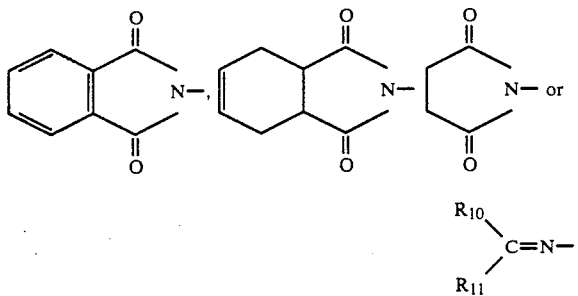

(in which $R_{10}$ and $R_{11}$, which may be the same or different, are a lower alkyl or phenyl group), to obtain a compound represented by formula (XII), $$Y-O-\overset{R_4}{\underset{|}{CH}}-\overset{R_5}{\underset{|}{C}}=\overset{R_6}{\underset{|}{C}}-C\equiv C-R_7 \qquad (XII)$$

wherein Y, $R_4$, $R_5$, $R_6$ and $R_7$ are the same as defined above, and reacting the resulting compound with, for example, hydroxylamine or hydrazine. Alternatively, the compound can be produced by reacting the resulting compound with, for example, a mineral acid (e.g. hydrochloric acid, sulfuric acid) and then neutralized.

When the compound of the formula (III) is reacted with the compound of the formula (XI), a solvent is usually used. Such solvents include amides (e.g. N,N-dimethylformamide, N,N-dimethylacetamide), sulfoxides (e.g. dimethyl sulfoxide, sulfolane), aromatic hydrocarbons (e.g. benzene, toluene, chlorobenzene), halogenated hydrocarbons (e.g. methylene chloride, chloroform, dichloroethane), alcohols (e.g. methanol, ethanol, isopropanol), nitriles (e.g. acetonitrile), pyridines (e.g. pyridine, picoline), water and mixtures thereof. Also, when this reaction is carried out, a base is usually used. Such bases include alkali metal hydroxides (e.g. lithium hydroxide, sodium hydroxide, potassium hydroxide), alkali metal carbonates (e.g. potassium carbonate, sodium carbonate), alkali metal hydrogencarbonates (e.g. sodium hydrogencarbonate), aliphatic amines (e.g. triethylamine), alkali metal alkoxides (e.g. sodium methylate, sodium ethylate), alkali metal hydrides (e.g. sodium hydride, potassium hydride), etc.

As to the amounts of the reagents used for reaction, the amount of the compound of the formula (XI) is from 0.1 to 10 moles, preferably from 0.5 to 2 moles based on 1 mole of the compound of the formula (III), and that of the base is from 0.5 to 10 moles based on the same. The reaction temperature is usually from $-30°$ to $200°$ C., preferably from $-0°$ to $150°$ C., and the reaction time is usually from 5 minutes to 100 hours, preferably from 30 minutes to 50 hours.

In addition for example a phase transfer catalyst such as ammonium salts (e.g. tetra-n-butylammonium bromide, benzyltrimethylammonium chloride), ethers (e.g. 18-Crown-6), tris(3,6-dioxoheptyl) amine (TDA-1), etc. may be used in an amount of from 0.0001 to 1 mole based on 1 mole of the compound of the formula (III).

After the completion of the reaction, the compound of the formula (XII) can be obtained by the usual after-treatments.

When the compound of the formula (XII) is reacted with hydroxylamine or hydrazine, or with a mineral acid (e.g. hydrochloric acid, sulfuric acid), a solvent is usually used. Such solvents include alcohols (e.g. methanol, ethanol, isopropanol), aromatic hydrocarbons (e.g. benzene, toluene, chlorobenzene), water and mixtures thereof.

The amount of hydroxylamine, hydrazine or a mineral acid (e.g. hydrochloric acid, sulfuric acid) used is from 0.5 to 100 moles based on 1 mole of the compound of the formula (XII). The reaction temperature is usually from $0°$ to $300°$ C., and the reaction time is usually from 5 minutes to 200 hours.

In addition a phase transfer catalyst such as ammonium salts (e.g. tetra-n-butylammonium bromide, benzyltrimethylammonium chloride), ethers (e.g. 18-Crown-6), tris(3,6-dioxoheptyl)amine (TDA-1), etc. may be used in an amount of from 0.0001 to 1 mole based on 1 mole of the compound of the formula (XII).

After the completion of the reaction, the desired compound of the formula (V) can be obtained by the liquid-liquid separation of the reaction solution, or purification and neutralization with an acid (e.g. hydrochloric acid, sulfuric acid) or a base (e.g. sodium hydroxide, potassium hydroxide).

The compound represented by the formula (IV) can be obtained, for example, by reacting a compound represented by the formula (XIII),

wherein $R_1$, $R_2$ and $R_3$ are the same as defined above, with a compound represented by the formula (XIV),

wherein $R_9$ is the same as defined above.

In carrying out this reaction, a solvent is not always necessary, but when a solvent is necessary the following are used: Ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), sulfolane, dimethyl sulfoxide, aromatic hydrocarbons (e.g. benzene, toluene, chlorobenzene), halogenated hydrocarbons (e.g. methylene chloride, chloroform), ketones (e.g. acetone, methyl isobutyl ketone), nitriles (e.g. acetonitrile), pyridines (e.g. pyridine, picoline), water and mixtures of these solvents. The compound of the formula (XIV) is used in an amount of from 0.5 to 10 moles based on 1 mole of the compound of the formula (XIII). The reaction temperature is usually from $-20°$ to $200°$ C., preferably from $-10°$ to $100°$ C. The reaction time is usually from 5 minutes to 100 hours, preferably from 30 minutes to 50 hours.

Usually, in carrying out this reaction, the following compounds are used as an acid-binding agent: Alkali metal hydroxides (e.g. lithium hydroxide, sodium hydroxide, potassium hydroxide), alkali metal carbonates (e.g. sodium carbonate, potassium carbonate), alkali metal hydrides (e.g. lithium hydride, sodium hydride, potassium hydride), alkali metals (e.g. metallic lithium, metallic sodium, metallic potassium), alkali metal alkoxides (e.g. sodium methoxide, sodium ethoxide) and mixtures thereof. The amount of the acid-binding agent used is from 0.5 to 10 moles based on 1 mole of the compound of the formula (XIII). If necessary, as a catalyst for the reaction, a phase transfer catalyst such as ammonium salts (e.g. tetra-n-butylammonium bromide, benzyltrimethylammonium chloride), ethers (e.g. 18-Crown-6), amines [e.g. tris(3,6dioxoheptyl)amine (TDA-1)], etc. may be used in an amount of from 0.0001 to 1 mole based on 1 mole of the compound of the formula (XIII).

After the completion of the reaction, the desired compound of the formula (IV) can be obtained by the usual after-treatments.

The compound represented by the formula (II) can be obtained by reacting the compound represented by the formula (IV) with a hydroxylamine/acid adduct such as hydroxylamine hydrochloride, hydroxylamine sulfate, etc.

In carrying out this reaction, a solvent is not always necessary, but when a solvent is required the following are used: Ethers (e.g. diethyl ether, tetrahydrofuran, dioxane), alcohols (e.g. ethylene glycol, glycerin, methanol, ethanol), acid amides (e.g. N,N-dimethylformamide, N,N-dimethylacetamide), sulfolane, dimethyl sulfoxide, aromatic hydrocarbons (e.g. benzene, toluene, chlorobenzene), halogenated hydrocarbons (e.g. methylene chloride, chloroform), aliphatic hydrocarbons (e.g. pentane, hexane, heptane, cyclohexane), pyridines (e.g. pyridine, picoline), acetic acid, water and mixtures of these solvents. The hydroxylamine/acid adduct is used in an amount of from 0.5 to 10 moles based on 1 mole of the compound of the formula (VII). The reaction temperature is usually from $-20°$ to $200°$ C., preferably from $-10°$ to $150°$ C. The reaction time is usually from 5 minutes to 100 hours, preferably from 5 minutes to 20 hours.

Usually, in carrying out this reaction, the following compounds are used as an acid-binding agent: Alkali metal hydroxides (e.g. lithium hydroxide, sodium hydroxide, potassium hydroxide), alkali metal carbonates (e.g. sodium carbonate, potassium carbonate), alkali metal hydrides (e.g. lithium hydride, sodium hydride, potassium hydride), alkali metals (e.g. metallic lithium, metallic sodium, metallic potassium), alkali metal alkoxides (e.g. sodium methoxide, sodium ethoxide) and mixtures thereof. The amount of the acid-binding agent used is from 0.5 to 10 moles based on 1 mole of the compound of the formula (IV). If necessary, as a catalyst for the reaction, a phase transfer catalyst such as ammonium salts (e.g. tetra-n-butylammonium bromide, benzyltrimethylammonium chloride), ethers (e.g. 18-Crown-6), amines [e.g. tris(3,6-dioxoheptyl)amine (TDA-1)], etc. may be used in an amount of from 0.0001 to 1 mole based on 1 mole of the compound of the formula (IV).

After the completion of the reaction, the desired compound of the formula (II) can be obtained by the usual after-treatments. The compounds represented by the formula (XIII), (XV), (XVI)

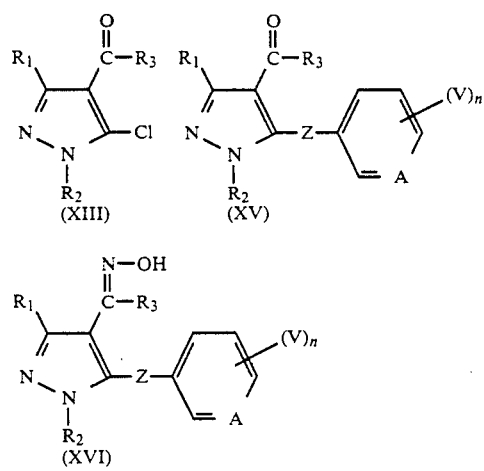

wherein $R_1$, $R_2$, $R_3$, A, V, Z and n are the same as defined, can be produced int he similar manner as described in EP-A2-234,045 and JP-A-64-13086.

The compounds shown in Table 1 are examples of the compounds represented by formula (I).

TABLE 1

Compounds represented by the formula:

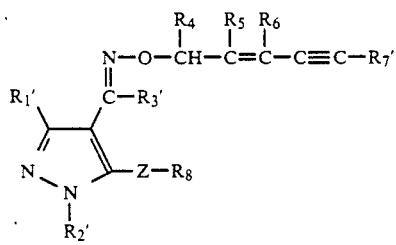

| $R_1'$ | $R_2'$ | $R_3'$ | $R_4$ | $R_5$ | $R_6$ | $R_7'$ | Z | $R_8$ |
|---|---|---|---|---|---|---|---|---|
| H | CH$_3$ | H | H | H | H | $-\underset{\underset{CH_3}{\mid}}{\overset{\overset{CH_3}{\mid}}{C}}-CH_3$ | O | phenyl |
| CH$_3$ | H | H | H | H | H | $-\underset{\underset{CH_3}{\mid}}{\overset{\overset{CH_3}{\mid}}{C}}-CH_3$ | O | phenyl |

TABLE 1-continued

Compounds represented by the formula:

$$\underset{\underset{R_{2}'}{N-N}}{\overset{R_{1}'}{\underset{\|}{\overset{}{C}}-\underset{R_{3}'}{\overset{N-O-CH-C=C-C\equiv C-R_{7}'}{\overset{R_4\ R_5\ R_6}{}}}}}-Z-R_8$$

| $R_1'$ | $R_2'$ | $R_3'$ | $R_4$ | $R_5$ | $R_6$ | $R_7'$ | Z | $R_8$ |
|---|---|---|---|---|---|---|---|---|
| CH$_3$ | CH$_3$ | CH$_3$ | H | H | H | $-\underset{\underset{CH_3}{\|}}{\overset{\overset{CH_3}{\|}}{C}}-CH_3$ | O | 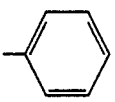 |
| CH$_3$ | CH$_3$ | 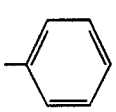 | H | H | H | $-\underset{\underset{CH_3}{\|}}{\overset{\overset{CH_3}{\|}}{C}}-CH_3$ | O | 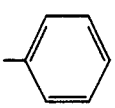 |
| 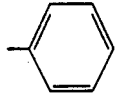 | CH$_3$ | H | H | H | H | $-\underset{\underset{CH_3}{\|}}{\overset{\overset{CH_3}{\|}}{C}}-CH_3$ | O | 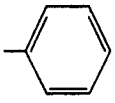 |
| CH$_3$ | CH$_3$ | H | H | H | H | $-\underset{\underset{CH_3}{\|}}{\overset{\overset{CH_3}{\|}}{C}}-CH_3$ | O | 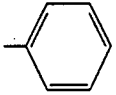 |
| CH$_3$ | CH$_3$ | H | H | CH$_3$ | H | $-\underset{\underset{CH_3}{\|}}{\overset{\overset{CH_3}{\|}}{C}}-CH_3$ | O | 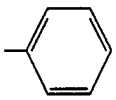 |
| CH$_3$ | CH$_3$ | H | H | H | H | 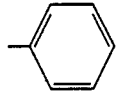 | O | 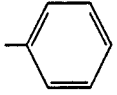 |
| CH$_3$ | CH$_3$ | H | CH$_3$ | H | H | $-\underset{\underset{CH_3}{\|}}{\overset{\overset{CH_3}{\|}}{C}}-CH_3$ | O | 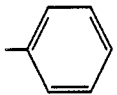 |
| CH$_3$ | CH$_3$ | H | H | H | CH$_3$ | $-\underset{\underset{CH_3}{\|}}{\overset{\overset{CH_3}{\|}}{C}}-CH_3$ | O | 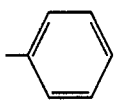 |
| CH$_3$ | —CH$_2$CH$_3$ | H | H | H | H | $-\underset{\underset{CH_3}{\|}}{\overset{\overset{CH_3}{\|}}{C}}-CH_3$ | O | 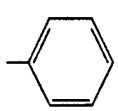 |
| —CH$_2$CH$_3$ | CH$_3$ | H | H | H | H | $-\underset{\underset{CH_3}{\|}}{\overset{\overset{CH_3}{\|}}{C}}-CH_3$ | O | 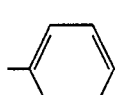 |
| CH$_3$ | CH$_3$ | H | CH$_3$ | CH$_3$ | H | 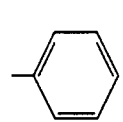 | O | 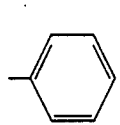 |

TABLE 1-continued

Compounds represented by the formula:

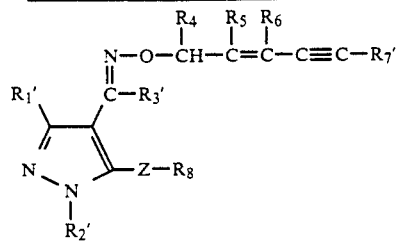

| $R_1'$ | $R_2'$ | $R_3'$ | $R_4$ | $R_5$ | $R_6$ | $R_7'$ | Z | $R_8$ |
|---|---|---|---|---|---|---|---|---|
| $CH_3$ | $CH_3$ | H | H | H | H | $-\underset{\underset{CH_3}{\mid}}{\overset{\overset{CH_3}{\mid}}{C}}-CH_3$ | S | phenyl |
| $CH_3$ | $CH_3$ | H | $CH_3$ | $CH_3$ | H | $-\underset{\underset{CH_3}{\mid}}{\overset{\overset{CH_3}{\mid}}{C}}-CH_3$ | O | phenyl |
| $CH_3$ | $CH_3$ | H | $CH_3$ | H | H | $-(CH_2)_{\overline{4}}CH_3$ | O | phenyl |
| $CH_3$ | $CH_3$ | H | H | $CH_3$ | H | cyclohexyl (H) | O | phenyl |
| $CH_3$ | $CH_3$ | H | $CH_3$ | H | H | $-\underset{\underset{CH_3}{\mid}}{\overset{\overset{CH_3}{\mid}}{C}}-CH_3$ | O | phenyl |
| $CH_3$ | $CH_3$ | H | (R4 and R6, taken together, form a six-membered ring, and R5 is a hydrogen atom). | | | $-\underset{\underset{CH_3}{\mid}}{\overset{\overset{CH_3}{\mid}}{C}}-CH_3$ | O | phenyl |
| $CH_3$ | $CH_3$ | H | H | H | H | $-\underset{\underset{CH_3}{\mid}}{\overset{\overset{CH_2CH_3}{\mid}}{C}}-CH_3$ | O | phenyl |
| $CH_3$ | $CH_3$ | H | H | H | H | $-\underset{\underset{CH_2CH_3}{\mid}}{\overset{\overset{CH_2CH_3}{\mid}}{C}}-CH_3$ | O | phenyl |
| $CH_3$ | $CH_3$ | H | H | H | H | $-\underset{\underset{CH_3}{\mid}}{\overset{\overset{CH_3}{\mid}}{CH}}$ | O | phenyl |
| $CH_3$ | $CH_3$ | H | H | H | H | cyclopentyl | O | phenyl |

TABLE 1-continued

Compounds represented by the formula:

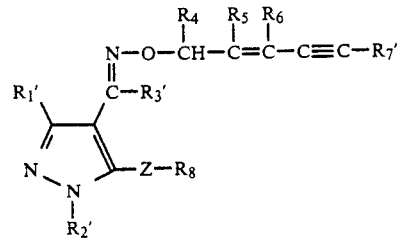

| R$_1'$ | R$_2'$ | R$_3'$ | R$_4$ | R$_5$ | R$_6$ | R$_7'$ | Z | R$_8$ |
|---|---|---|---|---|---|---|---|---|
| CH$_3$ | CH$_3$ | H | H | H | H | 1-methylcyclohexyl | O | phenyl |
| CH$_3$ | CH$_3$ | H | H | H | H | —CH$_2$CH$_3$ | O | phenyl |
| CH$_3$ | CH$_3$ | H | H | H | H | cyclohexyl | O | 3-fluorophenyl |
| CH$_3$ | CH$_3$ | H | H | H | H | —(CH$_2$)$_3$CH$_3$ | O | phenyl |
| CH$_3$ | CH$_3$ | H | H | H | H | cyclohexyl | O | 2-fluorophenyl |
| CH$_3$ | —CH(CH$_3$)$_2$ | H | H | H | H | —C(CH$_3$)$_3$ | O | phenyl |
| CH$_3$ | —(CH$_2$)$_3$CH$_3$ | H | H | H | H | —C(CH$_3$)$_3$ | O | phenyl |
| CH$_3$ | CH$_3$ | H | H | H | H | —C(CH$_3$)$_3$ | O | 4-chlorophenyl |
| CH$_3$ | CH$_3$ | H | H | H | H | —C(CH$_3$)$_3$ | O | 4-methoxyphenyl |
| CH$_3$ | CH$_3$ | H | H | H | H | —C(CH$_3$)$_3$ | O | 4-methylphenyl |

TABLE 1-continued

Compounds represented by the formula:

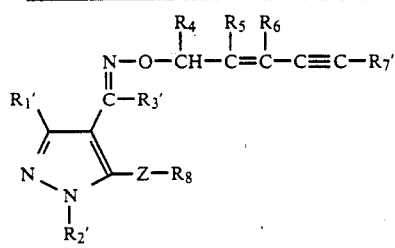

| $R_1'$ | $R_2'$ | $R_3'$ | $R_4$ | $R_5$ | $R_6$ | $R_7'$ | Z | $R_8$ |
|---|---|---|---|---|---|---|---|---|
| CH$_3$ | CH$_3$ | H | H | H | H | cyclohexyl | O | 4-F-phenyl |
| CH$_3$ | CH$_3$ | H | H | H | H | cyclohexyl | O | phenyl |
| CH$_3$ | CH$_3$ | H | CH$_3$ | H | CH$_3$ | -C(CH$_3$)$_3$ | O | phenyl |
| CH$_3$ | CH$_3$ | H | H | H | H | -(CH$_2$)$_2$-CH$_3$ | O | phenyl |
| CH$_3$ | CH$_3$ | H | H | H | H | -C(CH$_3$)$_3$ | O | 4-F-phenyl |
| CH$_3$ | CH$_3$ | H | H | H | H | -C(CH$_3$)$_3$ | O | 3-F-phenyl |
| CH$_3$ | CH$_3$ | H | H | H | H | -C(CH$_3$)$_3$ | O | 2-F-phenyl |
| CH$_3$ | -CH$_2$CH$_2$Cl | H | H | H | H | -C(CH$_3$)$_3$ | O | phenyl |
| CH$_3$ | CH$_3$ | H | H | H | H | -C(CH$_3$)$_3$ | O | 3,5-difluorophenyl |

TABLE 1-continued

Compounds represented by the formula:

$$\begin{array}{c} R_4 \quad R_5 \; R_6 \\ N-O-CH-C=C-C\equiv C-R_7' \\ \parallel \\ R_1' \quad C-R_3' \\ \diagup \quad \diagdown \\ N \qquad Z-R_8 \\ \diagdown \; \diagup \\ N \\ \vert \\ R_2' \end{array}$$

| $R_1'$ | $R_2'$ | $R_3'$ | $R_4$ | $R_5$ | $R_6$ | $R_7'$ | Z | $R_8$ |
|---|---|---|---|---|---|---|---|---|
| CH₃ | CH₃ | H | H | H | H | -C(CH₃)₃ | O | 3,5-dichlorophenyl |
| CH₃ | CH₃ | H | H | H | H | -C(CH₃)₃ | O | 3,5-dimethylphenyl |
| CH₃ | CH₃ | H | H | H | H | -C(CH₃)₃ | O | 3,4-methylenedioxyphenyl |
| CH₃ | CH₃ | H | H | H | H | -C(CH₃)₃ | O | 3-(CF₃)phenyl |
| CH₃ | CH₃ | H | H | H | H | -C(CH₃)₃ | O | 4-(OCF₂CF₂H)phenyl |
| CH₃ | CH₃ | H | H | H | H | -C(CH₃)₃ | O | 4-(OCF₂H)phenyl |
| CH₃ | CH₃ | H | CH₃ | H | H | -C(CH₃)₃ | O | 4-fluorophenyl |
| CH₃ | CH₃ | H | H | H | H | -C(CH₃)₃ | O | 4-chloro-3-methylphenyl |
| CH₃ | CH₃ | H | H | H | H | -C(CH₃)₃ | O | cyclohexyl |

TABLE 1-continued

Compounds represented by the formula:

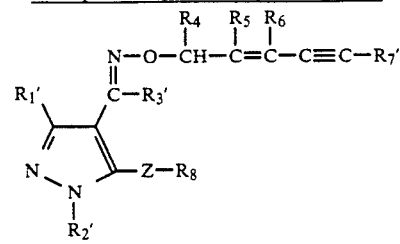

| R$_1$' | R$_2$' | R$_3$' | R$_4$ | R$_5$ | R$_6$ | R$_7$' | Z | R$_8$ |
|---|---|---|---|---|---|---|---|---|
| CH$_3$ | CH$_3$ | H | H | H | H | -C(CH$_3$)$_3$ | O | cyclopentyl (H) |
| CH$_3$ | CH$_3$ | H | H | H | H | -C(CH$_3$)$_3$ | O | -CH(CH$_3$)CH$_3$ |
| CH$_3$ | CH$_3$ | H | H | H | H | -C(CH$_3$)$_3$ | O | -CH$_2$CH$_2$CH$_2$CH$_3$ |
| CH$_3$ | CH$_3$ | H | H | H | H | -C(CH$_3$)$_3$ | O | 4-methylcyclohexyl (H, CH$_3$) |
| CH$_3$ | CH$_3$ | H | H | H | H | -C(CH$_3$)$_3$ | O | 3-methylcyclohexyl (H, CH$_3$) |
| CH$_3$ | CH$_3$ | H | H | H | H | -C(CH$_3$)$_3$ | O | 4-chlorocyclohexyl (H, Cl) |
| CH$_3$ | CH$_3$ | H | H | H | H | -C(CH$_3$)$_3$ | O | methylcyclopentyl (CH$_3$) |
| CH$_3$ | CH$_3$ | H | H | H | H | -C(CH$_3$)$_3$ | O | cyclopropyl |
| CH$_3$ | CH$_3$ | H | H | H | H | -C(CH$_3$)$_3$ | O | cycloheptyl |
| CH$_3$ | CH$_3$ | H | H | H | H | -C(CH$_3$)$_3$ | O | -CH(CH$_3$)C≡CH |
| CH$_3$ | CH$_3$ | H | H | H | H | -C(CH$_3$)$_3$ | O | -CH$_2$CH$_2$CH$_2$Cl |

TABLE 1-continued

Compounds represented by the formula:

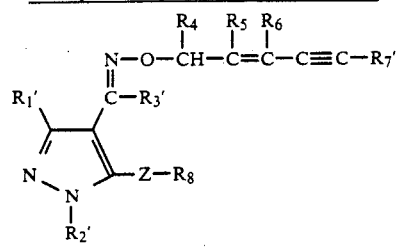

| $R_1'$ | $R_2'$ | $R_3'$ | $R_4$ | $R_5$ | $R_6$ | $R_7'$ | Z | $R_8$ |
|---|---|---|---|---|---|---|---|---|
| CH₃ | CH₃ | H | H | H | H | -C(CH₃)₃ | O | -CH₂CH₂OCH₃ |
| CH₃ | CH₃ | H | H | H | H | -C(CH₃)₃ | O | -CH₂CH₂SCH₃ |
| CH₃ | CH₃ | H | H | H | H | -C(CH₃)₃ | O | -CH₂CH₂N(CH₃)₂ |
| CH₃ | CH₃ | H | H | H | H | -C(CH₃)₃ | O | -CH₂C(Cl)=CH₂ |
| CH₃ | CH₃ | H | H | H | H | -C(CH₃)₃ | O | -(CH₂)₃-cyclohexyl |
| CH₃ | CH₃ | H | H | H | H | -C(CH₃)₃ | O | -CH₂CH₂CH₃ |
| CH₃ | CH₃ | H | H | H | H | -C(CH₃)₃ | O | -CH₂CH(CH₃)₂ |
| CH₃ | CH₃ | H | H | H | H | -C(CH₃)₃ | O | -CH(CH₃)(CH₂CH₃) |
| CH₃ | CH₃ | H | H | H | H | -C(CH₃)₃ | O | -CH₂C(CH₃)₃ |
| CH₃ | CH₃ | H | H | H | H | -C(CH₃)₃ | O | -CH(CH₃)CH=CH₂ |
| CH₃ | CH₃ | H | H | H | H | -C(CH₃)₃ | S | -cyclohexyl |

TABLE 1-continued

Compounds represented by the formula:

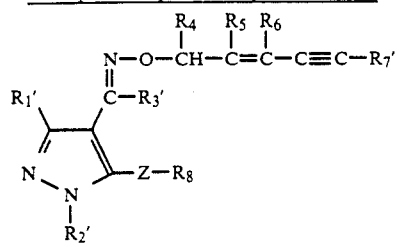

| R₁' | R₂' | R₃' | R₄ | R₅ | R₆ | R₇' | Z | R₈ |
|---|---|---|---|---|---|---|---|---|
| CH₃ | CH₃ | H | H | H | H | -C(CH₃)₃ | S | cyclopentyl |
| CH₃ | CH₃ | H | H | H | H | -C(CH₃)₃ | S | -CH(CH₃)₂ |
| CH₃ | CH₃ | H | H | H | H | -C(CH₃)₃ | O | 3-pyridyl |
| CH₃ | CH₃ | H | H | H | H | -C(CH₃)₃ | O | 2-pyridyl |
| CH₃ | CH₃ | H | H | H | H | -C(CH₃)₃ | O | -CH₂(CH₂)₄-CH₃ |
| CH₃ | CH₃ | H | H | H | H | -C(CH₃)₃ | O | tetrahydropyran-4-yl |
| CH₃ | CH₃ | H | H | H | H | -CH(CF₃)(CH₃) | O | phenyl |
| CH₃ | CH₃ | H | H | H | H | -CH(CF₃)(C₆H₅) | O | phenyl |
| CH₃ | CH₃ | H | H | H | H | -C(CH₃)₂(C₆H₅) | O | cyclohexadienyl |
| CH₃ | CH₃ | H | H | H | H | -C(CH₃)₂(OCH₃) | O | cyclohexyl |

TABLE 1-continued

Compounds represented by the formula:

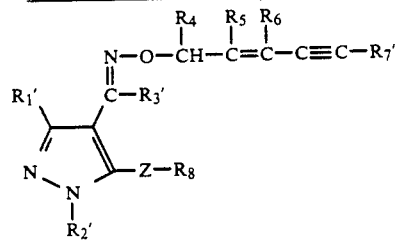

| R₁' | R₂' | R₃' | R₄ | R₅ | R₆ | R₇' | Z | R₈ |
|---|---|---|---|---|---|---|---|---|
| CH₃ | CH₃ | H | H | H | H | -CH(CF₃)(CH₃) | O | -CH(CH₃)₂ |
| CH₃ | CH₃ | H | H | H | H | -CH(CF₃)(CH₃) | S | -CH(CH₂CH₃)(CH₃) |
| -CH₂CH₃ | CH₃ | H | H | H | H | -C(CH₃)₃ | O | -CH(CH₃)₂ |
| -CH₂CH₃ | CH₃ | H | H | H | H | -C(CH₃)₃ | O | cyclohexyl |
| CH₃ | CH₃ | H | H | H | H | -C(CH₃)₃ | O | -(CH₂)₂SCH₂CH₃ |
| CH₃ | CH₃ | H | H | H | H | -C(CH₃)₂(OCH₃) | O | phenyl |
| CH₃ | CH₃ | H | H | H | H | -C(CH₃)₂(SCH₃) | O | phenyl |
| CH₃ | CH₃ | H | H | H | H | -C(CH₃)₂(CH₂Cl) | O | phenyl |
| CH₃ | CH₃ | H | H | H | H | -C(CH₃)₃ | S | -CH₂CH(CH₃)- |
| CH₃ | CH₃ | H | H | H | H | -C(CH₃)₃ | O | -CH(CH₃)CH₂CH₃ |
| CH₃ | CH₃ | H | H | H | H | -C(CH₃)₃ | O | -CH₂CF₃ |

TABLE 1-continued

Compounds represented by the formula:

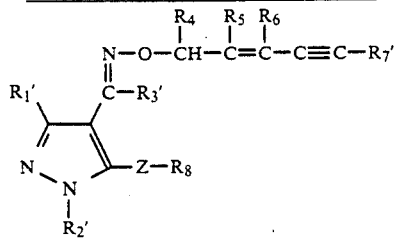

| R$_1'$ | R$_2'$ | R$_3'$ | R$_4$ | R$_5$ | R$_6$ | R$_7'$ | Z | R$_8$ |
|---|---|---|---|---|---|---|---|---|
| CH$_3$ | —CH$_2$CH$_3$ | H | H | H | H | —C(CH$_3$)$_3$ | O | —CH(CH$_3$)$_2$ |
| CH$_3$ | CH$_3$ | H | H | H | H | —C(CH$_3$)$_3$ | O | 2-methylcyclohexyl |
| CH$_3$ | CH$_3$ | H | H | H | H | —C(CH$_3$)$_3$ | O | —CH$_2$CH$_2$CH(CH$_3$)$_2$ |
| CH$_3$ | CH$_3$ | H | H | H | H | —C(CH$_3$)$_3$ | O | —CH(CH$_3$)CH$_2$OCH$_3$ |
| CH$_3$ | CH$_3$ | H | H | H | H | 2-pyridyl | O | phenyl |
| CH$_3$ | CH$_2$F | H | H | H | H | —C(CH$_3$)$_3$ | O | phenyl |
| CH$_3$ | CH$_3$ | H | H | H | H | —C(CH$_3$)$_3$ | O | —CH$_2$CF$_2$CF$_3$ |
| CH$_3$ | CH$_3$ | H | H | H | H | —C(CH$_3$)$_3$ | O | —CH$_2$CF$_2$CF$_2$CF$_3$ |

When compounds of formula (I) are used as an active ingredient for insecticidal and acaricidal compositions, the addition of any other ingredients is not necessary. Usually, however, the compounds are formulated into oil sprays, emulsifiable concentrates, wettable powders, flowable concentrates, granules, dusts, aerosols, poisonous baits, etc. by mixing with solid carriers, liquid carriers, gaseous carriers, baits and if necessary, surface active agents and other auxiliaries for formulation.

These formulations contain the compounds (I) as an active ingredient in an amount of, usually, from 0.01 to 95% by weight.

The solid carriers used in the formulation include fine powders or granules of clays (e.g. kaolin clay, diatomaceous earth, synthetic hydrated silicon dioxide, bentonite, Fubasami clay, terra abla), talcs, ceramics, other inorganic minerals (e.g. sericite, quartz, sulfur, activated carbon, calcium carbonate, hydrated silica), chemical fertilizers (e.g. ammonium sulfate, ammonium phosphate, ammonium nitrate, urea, ammonium chloride), etc. The liquid carriers include water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethyl sulfoxide, vegetable oils (e.g. soybean oil, cotton seed oil), etc. The gaseous carriers, i.e. propellants, include freon gas, butane gas, LPG (liquefied petroleum gas), dimethyl ether, carbon dioxide gas, etc.

The surface active agents used for the emulsification, dispersion, wetting, etc. include anionic surface active agents such as the salt of alkyl sulfates, alkyl(aryl)sulfonates, dialkyl sulfosuccinates, the salt of polyoxyethylene alkylaryl ether phosphoric acid esters, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc.

The auxiliaries for the formulation of the desired products such as fixing agents, dipersing agents, etc. include casein, gelatin, polysaccharides (e.g. starch powder, gum arabic, cellulose derivatives, alginic acid), lignin derivatives, bentonite, saccharides, synthetic water-soluble high polymers (e.g. polyvinyl alcohol, polyvinyl pyrrolidone, polyacrylic acids), etc. The stabilizing agents include PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surface active agents, fatty acids and their esters, etc.

The base for the poisonous baits includes bait components (e.g. grain powders, vegetable essential oils, saccharides, crystalline celluloses), antioxidants (e.g. dibutylhydroxytoluene, nordihydroguaiaretic acid), preservatives (e.g. dehydroacetic acid), attractants (e.g. cheese perfume, onion perfume), etc. Further, red pepper powders, etc. can be used as an agent to prevent children from the bait by mistake.

The flowable formulations (water-based suspension formulations or water-based emulsion formulations) are generally obtained by finely dispersing 1 to 75% of the active ingredient compounds in water containing 0.5 to 15% of a dispersing agent, 0.1 to 10% of a suspension auxiliary (e.g. protective colloids, or compounds giving a thixotropic property) and 0 to 10% of a suitable auxiliary (e.g. defoaming agents, anticorrosives, stabilizing agents, spreading agents, penetration auxiliaries, antifreezing agents, or antibacterial agents, antimolding agents). It is also possible to obtain oil-based suspension formulations by replacing the water by an oil in which the active ingredient compounds are almost insoluble. The protective colloids include gelatin, casein, gums, cellulose ethers, polyvinyl alcohol, etc. The compounds giving a thixotropic property include bentonite, aluminum magnesium silicate, xanthane gum, polyacrylic acid, etc.

The formulations thus obtained are used as the formulations are or diluted with water, etc. Further, they may be used mixed with other insecticides, acaricides, nematocides, soil-pest controlling agents, pest-controlling agents, fungicides, herbicides, plant growth regulators, synergists, fertilizers, soil improvers, etc., or may be used simultaneously with these chemicals without mixing.

When the compounds (I) are used as an active ingredient for agricultural insecticidal and acaricidal compositions, the dosage rate of the active ingredient is usually from 1 to 1,000 g/10 ares. When the emulsifiable concentrates, wettable powders, flowable concentrates, etc. are used diluted with water, the application concentration of the active ingredient is from 10 to 1,000 ppm. The granules, dusts, etc. are used as they are without being diluted. When the compounds are used as household and public hygienic insecticidal and acaricidal compositions, the emulsifiable concentrates, wettable powders, flowable concentrates, etc. are applied diluted with water to from 10 to 1,000 ppm, and the oil sprays, aerosols, poisonous baits, etc. are applied as they are.

Although any of these dosage rate and application concentration vary with the kind of formulations, when, where and how these formulations are applied, the kind of pests, the degree of damage, etc., they may be increased or decreased independently of the ranges explained above.

The present invention will be illustrated in more detail with reference to the following production examples, formulation examples and test examples, but it is not limited to these examples.

First, production examples of the compounds (I) will be shown.

PRODUCTION EXAMPLE 1 (METHOD A)

One gram (0.0043 mole) of 1,3-dimethyl-5-phenoxypyrazol-4-carboaldoxime was added to 10 ml of an N,N-dimethylformamide solution containing 0.1 g (0.0047 mole) of suspended sodium hydride, and the mixture was stirred at room temperature for 3 hours. Thereafter, 1.41 g (0.007 mole) of 1-bromo-6,6-dimethylhept-2-ene-4-yne was added with ice-cooling, and the mixture was stirred at room temperature for 3 hours. The reaction mixture was poured into 100 ml of ice water and extracted with three 50-ml portions of ethyl acetate. The organic layers were combined, washed once with 100 ml of a saturated aqueous sodium chloride solution, and dried over anhydrous magnesium sulfate, then concentrated under reduced pressure. The residue was subjected to column chromatography on silica gel to obtain 0.36 g of 1,3-dimethyl-5-phenoxypyrazol-4-carboaldoxime O-6,6-dimethylhept-2-ene-4-ynyl ether.

$N_D^{25.0}$ 1.5449.

PRODUCTION EXAMPLE 2 (METHOD B)

One gram (0.0064 mole) of 2,6,6-trimethylhepto-2-ene-4-ynyloxy amine was added to 10 ml of a methanol solution containing 1.38 g (0.0064 mole) of 1,3-dimethyl-4-formyl-5-phenoxypyrazole, a catalyzing amount of hydrogen chloride gas was flashed into the mixture, then the mixture was stirred at room temperature for 5 hours. The reaction mixture was poured into 100 ml of ice water and extracted with three 50-ml portions of ethyl acetate. The organic layers were combined, washed once with 100 ml of a saturated aqueous sodium chloride solution and dried over anhydrous magnesium sulfate, then concentrated under reduced pressure. The residue was subjected to column chromatography on silica gel to obtain 0.52 g of 1,3-dimethyl-5-phenoxypyrazol-4-carboaldoxime O-2,6,6-trimethylhept-2-ene-4-ynyl ether.

$n_D^{22.8}$ 1.5454.

Some of the compounds (I) thus obtained are shown in Table 2.

TABLE 2

Compounds represented by the formula:

| Compound No. | R1' | R2' | R3' | R4 | R5 | R6 | R7' | Z | R8 | Physical property |
|---|---|---|---|---|---|---|---|---|---|---|
| (1) | CH3 | CH3 | H | H | H | H | $-\underset{\underset{CH_3}{\mid}}{\overset{\overset{CH_3}{\mid}}{C}}-CH_3$ | O |  | $n_D^{25.0}$ 1.5449 |
| (2) | CH3 | CH3 | H | H | CH3 | H | $-\underset{\underset{CH_3}{\mid}}{\overset{\overset{CH_3}{\mid}}{C}}-CH_3$ | O |  | $n_D^{22.8}$ 1.5454 |
| (3) | CH3 | CH3 | H | H | H | H |  | O |  | $n_D^{23.0}$ 1.6091 |
| (4) | CH3 | CH3 | H | CH3 | H | H | $-\underset{\underset{CH_3}{\mid}}{\overset{\overset{CH_3}{\mid}}{C}}-CH_3$ | O |  | $n_D^{23.0}$ 1.5400 |
| (5) | CH3 | CH3 | H | H | H | CH3 | $-\underset{\underset{CH_3}{\mid}}{\overset{\overset{CH_3}{\mid}}{C}}-CH_3$ | O |  | $n_D^{23.6}$ 1.5412 |
| (6) | CH3 | CH3 | H | CH3 | H | CH3 | $-\underset{\underset{CH_3}{\mid}}{\overset{\overset{CH_3}{\mid}}{C}}-CH_3$ | O | 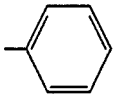 | $n_D^{25.0}$ 1.5317 |
| (7) | CH3 | CH3 | H | H | H | H | $-(CH_2)_{\overline{12}}CH_3$ | O |  | $n_D^{24.0}$ 1.5495 |
| (8) | CH3 | CH3 | H | H | H | H | $-\underset{\underset{CH_3}{\mid}}{\overset{\overset{CH_3}{\mid}}{C}}-CH_3$ | O | 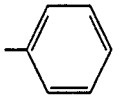 | $n_D^{25.5}$ 1.5350 |
| (9) | CH3 | CH3 | H | H | H | H | $-\underset{\underset{CH_3}{\mid}}{\overset{\overset{CH_3}{\mid}}{C}}-CH_3$ | O |  | $n_D^{25.5}$ 1.5352 |
| (10) | CH3 | CH3 | H | H | H | H | $-\underset{\underset{CH_3}{\mid}}{\overset{\overset{CH_3}{\mid}}{C}}-CH_3$ | O | 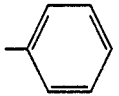 | $n_D^{26.0}$ 1.5375 |
| (11) | CH3 | CH3 | H | H | H | H | $-\underset{\underset{CH_3}{\mid}}{\overset{\overset{CH_3}{\mid}}{C}}-CH_3$ | O |  | $n_D^{26.0}$ 1.5492 |

TABLE 2-continued

Compounds represented by the formula:

| Compound No. | R₁' | R₂' | R₃' | R₄ | R₅ | R₆ | R₇' | Z | R₈ | Physical property |
|---|---|---|---|---|---|---|---|---|---|---|
| (12) | $CH_3$ | $CH_3$ | H | H | H | H | $-C(CH_3)_3$ | O | 4-$CH_3O$-phenyl | $n_D^{26.0}$ 1.5475 |
| (13) | $CH_3$ | $CH_3$ | H | H | H | H | $-C(CH_3)_3$ | O | 4-$CH_3$-phenyl | $n_D^{25.0}$ 1.5448 |
| (14) | $CH_3$ | $CH_3$ | H | H | H | H | cyclohexyl | O | 4-F-phenyl | $n_D^{26.5}$ 1.5515 |
| (15) | $CH_3$ | $CH_3$ | H | H | H | H | cyclohexyl | O | phenyl | $n_D^{26.5}$ 1.5629 |
| (16) | $CH_3$ | $CH_3$ | H | H | H | H | cyclohexyl | O | 3-F-phenyl | $n_D^{28.0}$ 1.5519 |
| (17) | $CH_3$ | $CH_3$ | H | H | H | H | $-(CH_2)_5CH_3$ | O | phenyl | $n_D^{26.5}$ 1.5459 |
| (18) | $CH_3$ | $CH_3$ | H | H | H | H | cyclohexyl | O | 2-F-phenyl | $n_D^{28.0}$ 1.5315 |
| (19) | $CH_3$ | $-CH(CH_3)_2$ | H | H | H | H | $-C(CH_3)_3$ | O | phenyl | $n_D^{27.5}$ 1.5385 |
| (20) | $CH_3$ | $-(CH_2)_3CH_3$ | H | H | H | H | $-C(CH_3)_3$ | O | phenyl | $n_D^{27.0}$ 1.5325 |
| (21) | $CH_3$ | $-CH_2CH_3$ | H | H | H | H | $-C(CH_3)_3$ | O | phenyl | $n_D^{27.0}$ 1.5388 |

TABLE 2-continued

Compounds represented by the formula:

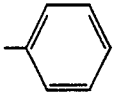

| Compound No. | $R_1'$ | $R_2'$ | $R_3'$ | $R_4$ | $R_5$ | $R_6$ | $R_7'$ | Z | $R_8$ | Physical property |
|---|---|---|---|---|---|---|---|---|---|---|
| (22) | —CH$_2$CH$_3$ | CH$_3$ | H | H | H | H | —C(CH$_3$)$_3$ | O | phenyl | mp 90.9° C. |
| (23) | CH$_3$ | CH$_3$ | H | CH$_3$ | CH$_3$ | H | phenyl | O | phenyl | $n_D^{25.0}$ 1.6002 |
| (24) | CH$_3$ | CH$_3$ | H | H | H | H | —C(CH$_3$)$_3$ | S | phenyl | mp 98.5° C. |
| (25) | CH$_3$ | CH$_3$ | H | CH$_3$ | CH$_3$ | H | —C(CH$_3$)$_3$ | O | phenyl | $n_D^{25.5}$ 1.5366 |
| (26) | CH$_3$ | CH$_3$ | H | CH$_3$ | H | H | —(CH$_2$)$_4$CH$_3$ | O | phenyl | $n_D^{25.5}$ 1.5517 |
| (27) | CH$_3$ | CH$_3$ | H | H | CH$_3$ | H | cyclohexyl | O | phenyl | $n_D^{25.5}$ 1.5518 |
| (28) | CH$_3$ | CH$_3$ | H | \multicolumn{3}{|}{($R_4$ and $R_6$, taken together, form a six-membered ring, and $R_5$ is a hydrogen atom).} | —C(CH$_3$)$_3$ | O | phenyl | $n_D^{26.5}$ 1.5412 |
| (29) | CH$_3$ | CH$_3$ | H | CH$_3$ | H | H | —C(CH$_3$)$_3$ | O | 4-F-phenyl | $n_D^{21.0}$ 1.5328 |
| (30) | CH$_3$ | CH$_3$ | H | H | H | H | —C(CH$_3$)$_3$ | O | 3-Cl-4-CH$_3$-phenyl | $n_D^{25.0}$ 1.5445 |
| (31) | CH$_3$ | CH$_3$ | H | H | H | H | —C(CH$_3$)$_3$ | O | cyclohexyl | $n_D^{23.0}$ 1.5278 |

TABLE 2-continued

Compounds represented by the formula:

$$\begin{array}{c} R_4 \quad R_5 \; R_6 \\ N-O-CH-C=C-C\equiv C-R_7' \\ R_1' \quad \| \\ C-R_3' \\ N \diagdown \quad Z-R_8 \\ N \\ | \\ R_2' \end{array}$$

| Compound No. | $R_1'$ | $R_2'$ | $R_3'$ | $R_4$ | $R_5$ | $R_6$ | $R_7'$ | Z | $R_8$ | Physical property |
|---|---|---|---|---|---|---|---|---|---|---|
| (32) | $CH_3$ | $CH_3$ | H | H | H | H | $-C(CH_3)_3$ | O | cyclopentyl | $n_D^{25.0}$ 1.5215 |
| (33) | $CH_3$ | $CH_3$ | H | H | H | H | $-C(CH_3)_3$ | O | $-CH(CH_3)_2$ | $n_D^{24.0}$ 1.5141 |
| (34) | $CH_3$ | $CH_3$ | H | H | H | H | $-C(CH_3)_3$ | O | $-CH_2CH_2CH_2CH_3$ | $n_D^{24.0}$ 1.5115 |
| (40) | $CH_3$ | $-C_2H_5$ | H | H | H | H | $-C(CH_3)_3$ | O | $-CH(CH_3)_2$ | $n_D^{21.0}$ 1.5108 |
| (41) | $CH_3$ | $CH_3$ | H | H | H | H | $-C(CH_3)_3$ | O | 2-methylcyclohexyl | $n_D^{21.0}$ 1.5225 |
| (42) | $CH_3$ | $CH_3$ | H | H | H | H | $-C(CH_3)_3$ | O | $-CH_2CH_2CH(CH_3)_2$ | $n_D^{21.0}$ 1.5060 |
| (43) | $CH_3$ | $CH_3$ | H | H | H | H | $-C(CH_3)_3$ | O | $-CH(CH_3)CH_2OCH_3$ | $n_D^{23.0}$ 1.5125 |
| (44) | $CH_3$ | $CH_3$ | H | H | H | H | $-C(CH_3)_3$ | S | $-CH(CH_3)_2$ | $n_D^{21.0}$ 1.5395 |
| (45) | $-CH_2CH_3$ | $CH_3$ | H | H | H | H | $-C(CH_3)_3$ | O | $-CH(CH_3)_2$ | $n_D^{23.0}$ 1.5239 |
| (46) | $-CH_2CH_3$ | $CH_3$ | H | H | H | H | $-C(CH_3)_3$ | O | cyclohexyl | $n_D^{23.0}$ 1.5104 |
| (47) | $CH_3$ | $CH_3$ | H | H | H | H | $-C(CH_3)_3$ | S | cyclohexyl | $n_D^{22.5}$ 1.5435 |

TABLE 2-continued

Compounds represented by the formula:

$$\begin{array}{c} R_1' \\ \diagdown \\ N \diagdown \diagup \overset{\overset{\displaystyle C-R_3'}{\|}}{\underset{\displaystyle N}{N}} \diagup Z-R_8 \\ | \\ R_2' \end{array} \quad \begin{array}{c} R_4 \; R_5 \; R_6 \\ | \; | \; | \\ N-O-CH-C=C-C\equiv C-R_7' \end{array}$$

| Compound No. | $R_1'$ | $R_2'$ | $R_3'$ | $R_4$ | $R_5$ | $R_6$ | $R_7'$ | Z | $R_8$ | Physical property |
|---|---|---|---|---|---|---|---|---|---|---|
| (48) | $CH_3$ | $CH_3$ | H | H | H | H | $-\underset{\underset{CH_3}{\vert}}{\overset{\overset{CH_3}{\vert}}{C}}-CH_3$ | O | $-CH_2CH_2SCH_2CH_3$ | $n_D^{24.0}$ 1.5329 |
| (49) | $CH_3$ | $CH_3$ | H | H | H | H | $-\underset{\underset{CH_3}{\vert}}{\overset{\overset{CH_3}{\vert}}{C}}-CH_3$ | O | 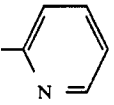 | $n_D^{23.0}$ 1.5402 |
| (50) | $CH_3$ | $CH_3$ | H | H | H | H | $-\underset{\underset{CH_3}{\vert}}{\overset{\overset{CH_3}{\vert}}{C}}-CH_3$ | O | 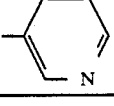 | $n_D^{22.0}$ 1.5455 |

PRODUCTION EXAMPLE 3 (PRODUCTION OF THE INTERMEDIATE)

Ten grams (0.122 mole) of 3,3-dimethyl-1-butyne was dissolved in 100 ml of anhydrous tetrahydrofuran, and the resulting solution was cooled to −40° C. or less in a dry ice-acetone bath. Under a stream of a nitrogen gas, 81.13 ml (0.122 mole) of a 1.5 M hexane solution of n-butyllithium was added dropwise at −40° C. or less with stirring. After aging the reaction solution at −50° C. for 30 minutes, 6.84 g (0.122 mole) of acrolein was added dropwise at −50° C. or less. After the reaction solution was allowed to stand overnight at room temperature, it was poured into 200 ml of ice water and extracted with two 100-ml portions of ethyl acetate. The organic layers were combined, washed once with 100 ml of a saturated aqueous sodium chloride solution and concentrated under reduced pressure. The resulting oily product was distilled under reduced pressure to obtain 125 g of 3-hydroxy-6,6-dimethylhept-1-ene-4-yne (bp$_{20}$, 80° C.).

Ten grams (0.072 mole) of 3-hydroxy-6,6-dimethylhept-1-ene-4-yne was dissolved in 100 ml of hexane, and to the resulting solution were added 50 mg (6.8×10$^{-4}$ mole) of N,N-dimethylformamide and 12.80 g (0.108 mole) of thionyl chloride. The mixture was reacted overnight at room temperature with stirring with a hydrogen chloride gas trap mounted on the reactor. The reaction mixture was concentrated under reduced pressure to obtain 10 g of a crude 1-chloro-6,6-dimethylhept-2-ene-4-yne.

PRODUCTION EXAMPLE 4

1.87 grams (0.0115 mole) of N-hydroxyphthalimide was dissolved in 20 ml of N,N-dimethylformamide, and 1.80 g (0.0115 mole) of the crude 1-chloro-6,6-dimethylhept-2-ene-4-yne and 1.28 g (0.0127 mole) of triethylamine were added to the resulting solution. The mixture was reacted at 25° C. for 15 hours with stirring. The reaction mixture was poured into 200 ml of ice water and extracted with two 100-ml portions of ethyl acetate. The organic layers were combined, washed once with 100 ml of a saturated aqueous sodium chloride solution and dried over anhydrous magnesium sulfate, then concentrated under reduced pressure. The residue was subjected to column chromatography on silica gel to obtain 0.72 g of a crude N-hydroxyphthalimide O-6,6-dimethylhept-2-ene-4-ynyl ether.

0.48 grams (1.7×10$^{-3}$ mole) of N-hydroxyphthalimide O-6,6-dimethylhept-2-ene-4-ynyl ether was dissolved in 10 ml of toluene, and 0.24 g (3.4×10$^{-3}$ mole) of hydroxylamine hydrochloride, 10 ml of water and 28 mg (8.5×10$^{-5}$ mole) of tetra-n-butylammonium bromide were added to the resulting mixture. The reaction solution was violently stirred, and 4.1 ml of a 5% aqueous sodium hydroxide solution was added dropwise at room temperature. After aging the solution at room temperature for 10 hours with stirring, the solution was separated into two layers. The aqueous layer was extracted once with 50 ml of toluene. The organic layers were combined and washed with 50 ml of a saturated aqueous sodium chloride solution. The organic layer was dried over anhyrous magnesium salfate and concentrated under reduced pressure to obtain 0.11 g of a crude hydroxylamine O-6,6-dimethylhept-2-ene-4ynyl ether.

$N_D^{25.0}$ 1.4878.

Thus, compounds of the formula (V) shown in Table 3 can be obtained in a similar manner.

TABLE 3

Compounds represented by the formula:

$$H_2N-O-\overset{R_4}{\underset{}{C}H}-\overset{R_5}{\underset{}{C}}=\overset{R_6}{\underset{}{C}}-C\equiv C-R_7$$

| R₄ | R₅ | R₆ | R₇ | Physical property |
|---|---|---|---|---|
| H | H | H | -C(CH₃)₃ | $n_D^{25.0}$ 1.4878 |
| CH₃ | H | H | -C(CH₃)₃ | $n_D^{25.0}$ 1.4861 |
| H | CH₃ | H | -C(CH₃)₃ | |
| H | H | CH₃ | -C(CH₃)₃ | |
| CH₃ | CH₃ | H | -C(CH₃)₃ | $n_D^{24.3}$ 1.4828 |
| CH₃ | H | CH₃ | -C(CH₃)₃ | |
| H | CH₃ | CH₃ | -C(CH₃)₃ | |
| CH₃ | CH₃ | CH₃ | -C(CH₃)₃ | |
| H | -CH₂CH₃ | H | -C(CH₃)₃ | |
| H | H | H | cyclohexyl (with H) | $n_D^{25.0}$ 1.5229 |
| H | H | H | -CH(CH₃)₂ | |
| H | H | H | -C(CH₃)(CH₂CH₃)... -C(CH₃)₃ variant (CH₂CH₃ / CH₃ / CH₃) | |
| H | H | H | ⁺(CH₂)₃CH₃ | |
| H | H | H | -CH₂CH₃ | |
| H | H | H | -C(CH₃)(CH₂CH₃)(CH₂CH₃) | |
| H | H | H | cyclopentyl | |
| H | H | H | cyclohexyl (CH₃, H substituents) | |
| H | H | H | cyclopropyl | |
| H | H | H | phenyl | $n_D^{24.2}$ 1.6192 |
| H | H | H | 4-Cl-phenyl | |
| H | H | H | 4-F-phenyl | |
| H | H | H | 4-CH₃-phenyl | |
| H | H | H | 4-OCH₃-phenyl | |
| H | H | H | ⁺(CH₂)₅CH₃ | |
| R₄ and R₆, taken together, form a six-membered ring, and R₅ is a hydrogen atom | | | -C(CH₃)₃ | |

PRODUCTION EXAMPLE 5

Under a nitrogen gas atmosphere, 3.48 g (0.0347 mole) of cyclohexanol was added at 0° C. to 50 ml of an N,N-dimethylformamide solution containing 1.45 g (0.03625 mole) of suspended sodium hydride. The resulting mixture was stirred at 0° C. for 1 hour. Thereafter, a solution of 5 g (0.0315 mole) of 5-chloro-1,3-dimethyl-4-formylpyrazole in 20 ml of N,N-dimethylformamide was added dropwise at 20° C. over 1 hour. The reaction mixture was stirred at 20° C. for 5 hours and then poured into 300 ml of ice water and extracted with two 100-ml portions of ethyl acetate. The organic layers were combined, washed once with 100 ml of a saturated aqueous sodium chloride solution, and dried over anhydrous magnesium sulfate, then concentrated under reduced pressure. The residue was subjected to column chromatography on silica gel to obtain 0.3 g of 1,3-dimethyl-5-cyclohexyloxy-4-formylpyrazole.

$n_D^{25.4}$ 1.5194.

Thus, compounds of the formula (IV) shown in Table 4 can be obtained in a similar manner.

TABLE 4

Compounds represented by the formula:

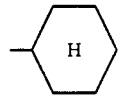

| $R_1$ | $R_2$ | $R_9$ | Physical property |
|---|---|---|---|
| $CH_3$ | $CH_3$ | 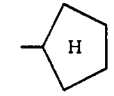 | $n_D^{25.4}$ 1.5194 |
| $CH_3$ | $CH_3$ | 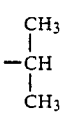 | $n_D^{25.0}$ 1.5180 |
| $CH_3$ | $CH_3$ | $\begin{array}{c} CH_3 \\ | \\ -CH \\ | \\ CH_3 \end{array}$ | $n_D^{25.0}$ 1.4959 |
| $CH_3$ | $CH_2CH_2Cl$ | 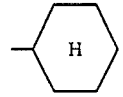 | |
| $CH_3$ | $CH_3$ | $\begin{array}{c} CH_2CH_3 \\ | \\ -CH \\ | \\ CH_3 \end{array}$ | |
| $CH_3$ | $CH_3$ | $\begin{array}{c} CH_2CH_3 \\ | \\ -CH \\ | \\ CH_2CH_3 \end{array}$ | |
| $CH_3$ | $CH_3$ | $\begin{array}{c} CH_3 \\ | \\ -CH_2CH \\ | \\ CH_3 \end{array}$ | |
| $CH_3$ | $CH_3$ | 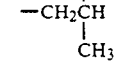 | |
| $CH_3$ | $CH_3$ |  | |
| $CH_3$ | $CH_3$ | 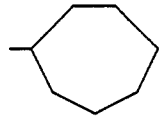 | |
| $CH_3$ | $CH_3$ | $-(CH_2)_3CH_3$ | |

TABLE 4-continued

Compounds represented by the formula:

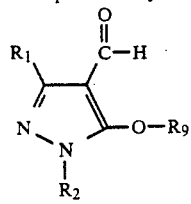

| R₁ | R₂ | R₉ | Physical property |
|---|---|---|---|
| CH₃ | CH₃ | —CH₂(CH₂)₄CH₃ | |
| CH₃ | CH₃ | —CH₂C(CH₃)₂CH₃ (with CH₃) | |
| CH₃ | CH₃ | 4-methylcyclohexyl | $n_D^{26.0}$ 1.5062 |
| CH₃ | CH₃ | 3-methylcyclohexyl | |
| CH₃ | CH₃ | 2-methylcyclohexyl | $n_D^{25.0}$ 1.5158 |
| CH₃ | CH₃ | methylcyclopentyl | |
| CH₃ | CH₃ | —CH(CH₃)CH=CH₂ | $n_D^{25.0}$ 1.5112 |
| CH₃ | CH₃ | tetrahydropyranyl (O) | |
| CH₃ | CH₃ | tetrahydrothiopyranyl (S) | |
| H | CH₃ | cyclopentyl | |
| —CH₂CH₃ | CH₃ | —CH(CH₂CH₃)CH₃ | |
| CH₃ | CH₃ | —CH₂CH₂OCH₃ | $n_D^{25.0}$ 1.5295 |
| CH₃ | CH₃ | —CH₂CH₂SCH₃ | |
| CH₃ | CH₃ | —CH₂CH₂CH₂Cl | |
| CH₃ | CH₃ | —CH₂CF₃ | $n_D^{24.0}$ 1.4611 |

TABLE 4-continued

Compounds represented by the formula:

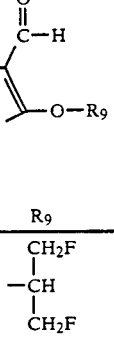

| $R_1$ | $R_2$ | $R_9$ | Physical property |
|---|---|---|---|
| $CH_3$ | $CH_2$ | $-CH(CH_2F)_2$ | $n_D^{24.0}$ 1.4933 |
| $-CH_2CH_3$ | $CH_3$ | cyclohexyl | $n_D^{27.5}$ 1.4927 |
| $-CH_2CH_3$ | $CH_3$ | $-CH(CH_3)_2$ | $n_D^{24.0}$ 1.5065 |
| $CH_3$ | $CH_3$ | $-CH(CH_3)CF_2CF_3$ | $n_D^{20.0}$ 1.4331 |
| $CH_3$ | $CH_3$ | $-CH_2CF_2CF_3$ | $n_D^{22.5}$ 1.4425 |
| $CH_3$ | $CH_3$ | $-CH_2CH_2SC_2H_5$ | $n_D^{25.0}$ 1.5335 |
| $CH_3$ | $CH_3$ | $-CH_2CH_2CH=CHCH_2CH_2Cl$ | |

PRODUCTION EXAMPLE 6

Five grams (0.0225) mole) of ,3-dimethyl-5-cyclohexyloxy-4-formylpyrazole was dissolved in 50 ml of pyridine at room temperature. 2.35 g (0.338 mole) of hydroxylamine hydrochloride, was added to the resulting mixture which, was stirred at room temperature for 5 hours. The reaction solution was poured into 200 ml of water, and the precipitated crystals were collected by filtration. The crystals were dried under reduced pressure to obtain 2.0 g of 1,3-dimethyl-5-cyclohexyloxypyrazol-4-carboaldoxime.

m.p. 107–109° C.

Thus, compounds of the formula (VI) shown in Table 5 can be obtained in a similar manner.

TABLE 5

Compounds represented by the formula:

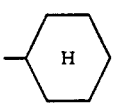

| $R_1$ | $R_2$ | $R_9$ | Physical property |
|---|---|---|---|
| $CH_3$ | $CH_3$ | cyclopentyl | m.p. 93–94° C. |
| $CH_3$ | $CH_3$ | $-CH(CH_3)_2$ | m.p. 121–122° C. |
| $CH_3$ | $CH_3$ | $-CH(CH_3)CH_2CH_3$ | m.p. 96–97° C. |

TABLE 5-continued

Compounds represented by the formula:

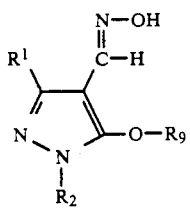

| R₁ | R₂ | R₉ | Physical property |
|---|---|---|---|
| CH₃ | CH₃ | —CH(CH₂CH₃)CH₂CH₃ | |
| CH₃ | CH₂CH₂Cl | cyclohexyl | |
| CH₃ | CH₃ | —CH₂—CH(CH₃)CH₃ | |
| CH₃ | CH₃ | cyclopropyl | |
| CH₃ | CH₃ | cycloheptyl | |
| CH₃ | CH₃ | bicyclic cyclohexyl-(CH₂)₃ | |
| CH₃ | CH₃ | ⁻(CH₂)₁₃CH₃ | m.p. 100–101° C. |
| CH₃ | CH₃ | —CH₂(CH₂)₁₄CH₃ | m.p. 56–57° C. |
| CH₃ | CH₃ | —CH₂C(CH₃)₂CH₃ | |
| CH₃ | CH₃ | 4-methylcyclohexyl | m.p. 101–102° C. |
| CH₃ | CH₃ | 3-methylcyclohexyl | |
| CH₃ | CH₃ | 2-methylcyclohexyl | m.p. 98.0–99.0° C. |
| CH₃ | CH₃ | 3-methylcyclopentyl | |

TABLE 5-continued

Compounds represented by the formula:

$$\begin{array}{c} \text{R}^1 \\ \diagup \\ \text{N} \\ | \\ \text{R}_2 \end{array} \begin{array}{c} \text{N}-\text{OH} \\ \| \\ \text{C}-\text{H} \\ \diagdown \\ \text{O}-\text{R}_9 \end{array}$$

| $R_1$ | $R_2$ | $R_9$ | Physical property |
|---|---|---|---|
| $CH_3$ | $CH_3$ | $-\underset{CH_3}{\underset{|}{CH}}-C\equiv CH$ | |
| $CH_3$ | $CH_3$ | $-\underset{CH_3}{\underset{|}{CH}}-CH=CH_2$ | |
| $CH_3$ | $CH_3$ | tetrahydropyran-4-yl (O) | |
| $CH_3$ | $CH_3$ | tetrahydrothiopyran-4-yl (S) | |
| H | $CH_3$ | cyclopentyl | |
| $-CH_2CH_3$ | $CH_3$ | $-\underset{CH_3}{\underset{|}{CH}}-CH_2CH_3$ | |
| $CH_3$ | $CH_3$ | $-CH_2CH_2OCH_3$ | m.p. 83.0–85.0° C. |
| $CH_3$ | $CH_3$ | $-CH_2CH_2SCH_3$ | |
| $CH_3$ | $CH_3$ | $-CH\begin{array}{c}CH_3\\ \diagdown CH_2OCH_3\end{array}$ | m.p. 55–56° C. |
| $CH_3$ | $CH_3$ | $-CH_2CH_2CH_2Cl$ | |
| $CH_3$ | $CH_3$ | $-CH_2CF_3$ | m.p. 151.0–152.0° C. |
| $CH_3$ | $CH_3$ | $-CH_2CH_2CH=CHCH_2CH_2Cl$ | |
| $CH_3$ | $CH_3$ | $-CH_2CF_2CF_3$ | m.p. 117–118° C. |
| $CH_3CH_2$ | $CH_3$ | $-CH_2CF_2CF_3$ | m.p. 113–114° C. |
| $CH_3$ | $CH_3$ | $-CH\begin{array}{c}CH_3\\ \diagdown CF_3\end{array}$ | m.p. 138–139° C. |
| $CH_3$ | $CH_3$ | $-CH\begin{array}{c}CH_3\\ \diagdown CF_2CF_3\end{array}$ | m.p. 125–126° C. |
| $CH_3$ | $CH_3$ | $-CH\begin{array}{c}CH_3\\ \diagdown CF_2CF_2CF_3\end{array}$ | m.p. 116–117° C. |

PRODUCTION EXAMPLE 7 (PRODUCTION OF THE INTERMEDIATE)

Under a nitrogen gas atmosphere, 3.0 g (0.032 mole) of 2-hydroxypyridine was added at 25° C. to 30 ml of a N,N-dimethylformamide solution containing 1.92 g (0.048 mole) of sodium hydroxide. Then, 5.1 g (0.032 mole) of 5-chloro-1,3-dimethyl-4-formylpyrazole in 20 ml of N,N-dimethylformamide was added to the mixture solution at 25° C. The reaction mixture was heated to 100° C. and stirred at 100° C. for 4 hours. The reaction mixture was then poured into 300 ml of ice water and extracted with two 100-ml portion of ethyl acetate. The organic layers were combined, washed once with 100 ml of saturated aqueous sodium chloride solution and dried over anhydrous magnesium sulfate, then concentrated under reduced pressure. The residue was subjected to column chromatography on silica gel to obtain 0.55 g of 1,3-dimethyl-5-(2-pyridyloxy)-4-formylpyrazole.

m.p. 56.0-57.0° C.

Formulation examples will be shown. In the examples, parts are by weight, and the present compounds employed hereinafter are shown by Compound Nos. in Table 2.

FORMULATION EXAMPLE 1

Ten parts of each of the compounds (1) to (50), 14 parts of polyoxyethylene styrylphenyl ether, 6 parts of calcium dodecylbenzenesulfonate, 35 parts of xylene and 35 parts of DMF are well mixed to obtain an emulsifiable concentrate of each compound.

FORMULATION EXAMPLE 2

0.2 parts of each of the compounds (1) to (7), 2 parts of xylene, 2 parts of DMF and 95.8 parts of kerosene are mixed to obtain an oil spray of each compound.

FORMULATION EXAMPLE 3

Twenty parts of each of the compounds (1), (15), (31), (32), 10 parts of Fenitrothion, 3 parts of calcium lignosulfonate, 2 parts of sodium lauryl sulfate and 65 parts of synthetic hydrated silicon dioxide are well pulverized and mixed to obtain a wettable powder of each compound.

FORMULATION EXAMPLE 4

One part of each of the compounds (1), (15), (31), (32), 2 parts of Carbaryl, 87 parts of kaolin clay and 10 parts of talc are well pulverized and mixed to obtain a dust of each compound.

FORMULATION EXAMPLE 5

Five parts of each of the compounds (1) to (7), (15), (31), (32), 1 part of synthetic hydrated silicon dioxide, 2 parts of calcium lignosulfonate, 30 parts of bentonite and 62 parts of kaolin clay are well pulverized and mixed. The resulting mixture is well kneaded with water, granulated and dried to obtain a granule of each compound.

FORMULATION EXAMPLE 6

0.05 parts of the compound (1), 0.2 parts of Tetramethrin, 0.05 parts of Resmethrin, 7 parts of xylene and 42.7 parts of deodorized kerosene are mixed into a solution. The solution is filled into an aerosol container. After mounting a valve portion on the container, 50 parts of a propellant (liquefied petroleum gas) are charged into the container under pressure through the valve portion to obtain an aerosol.

Test examples will be shown. The present compounds are shown by Compound Nos. in Table 2, and compounds used as a control are shown by Compound symbols in Table 6.

TABLE 6

| Compound symbol | Structural formula | Remarks |
|---|---|---|
| (A) | 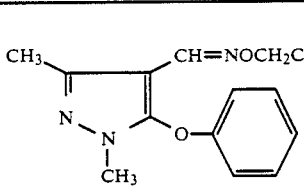 | Compound No. 800 described in EP No. 234045A2. |
| (B) | 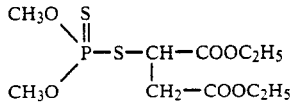 | Malathion |

TEST EXAMPLE 1

INSECTICIDAL TEST ON PESTICIDES-RESISTANT GREEN RICE LEAFHOPPER (*Nephotettix cincticeps*)

Each test compound was formulated into an emulsifiable concentrate according to Formulation example 1, and rice stems (length, about 12 cm) were dipped for minute into a 200-fold aqueous dilute solution (500 ppm) of the emulsifiable concentrate. After air-drying, the rice stems were put in a test tube, and 10 adults of resistant green rice leafhopper were freed into the test tube. After one day, the number of dead and alive adults were examined to obtain a mortality. This test was repeated twice.

The results are shown in Table 7.

TABLE 7

| Test compound | Mortality (%) |
|---|---|
| (1) | 100 |
| (8) | 100 |
| (A) | 0 |
| (B) | 50 |
| No treatment | 0 |

TEST EXAMPLE 2

INSECTICIDAL TEST ON GERMAN COCKROACH (*Blattella germanica*)

On the bottom of a polyethylene cup of 5.5 cm in diameter was placed a filter paper of the same size as a bottom, and 0.7 ml of the 200-fold aqueous dilute solution (500 ppm) of the emulsifiable concentrate, prepared from each test compound according to Formulation example 1, was dropped down to the filter paper. About mg of sucrose was put into the cup as a bait, and two male adults of German cockroach were freed into the cup. Six days after covering the cup, the number of dead and alive adults were examined to obtain a mortality. The results are shown in Table 8.

TABLE 8

| Test compound | Mortality (%) |
|---|---|
| (1) | 100 |
| (8) | 100 |
| (9) | 100 |
| (A) | 0 |
| No treatment | 0 |

TEST EXAMPLE 3

INSECTICIDAL TEST ON TOBACCO CUTWORM (*Spodoptera litura*)

Each test compound was formulated into an emulsifiable concentrate according to Formulation example 1, and 2 ml of a 200-fold aqueous dilute solution (500 ppm) of the emulsifiable concentrate was impregnated into 13 g of artificial feeds for tobacco cutworm previously prepared in a polyethylene cup of 11 cm in diameter. Ten fourth instar larvae of tobacco cutworm were freed into the cup. After six days, the number of dead and alive larvae were examined to obtain a mortality. This test was repeated twice. At the same time, the degree of attack upon the artificial feeds was also examined. The degree of attack was judged based on the following standard:

—: Little attack is observed.
+: Attack is observed.
++: Attack is heavy, few artificial feeds being left.

The results are shown in Table 9.

TABLE 9

| Test compound | Mortality (%) | Degree of attack |
|---|---|---|
| (1) | 100 | — |
| (2) | 100 | — |
| (7) | 100 | — |
| (8) | 100 | — |
| (9) | 100 | — |
| (11) | 100 | — |
| (12) | 100 | — |
| (13) | 100 | — |
| (14) | 100 | — |
| (15) | 100 | — |
| (16) | 100 | — |
| (17) | 100 | — |
| (22) | 100 | — |
| (27) | 100 | — |
| (31) | 100 | — |
| (32) | 100 | — |
| (35) | 100 | — |
| (36) | 100 | — |
| (37) | 100 | — |
| (39) | 100 | — |
| (41) | 100 | — |
| (42) | 100 | — |
| (45) | 100 | — |
| (47) | 100 | — |
| (49) | 100 | — |
| (A) | 30 | ++ |
| No treatment | 0 | ++ |

TEXT EXAMPLE 4

ACARICIDAL TEST ON CARMINE SPIDER MITE (*Tetranychus cinnabarinus*)

The female adults of carmine spider mite were parasitized, at a rate of 10 adults/leaf, a potted kidney bean (in the primary leaf stage) which had been seeded 7 days earlier, and placed under a constant-temperature of 25° C. After 6 days, the emulsifiable concentrate of each test compound prepared according to Formulation example 1 was diluted with water to an active ingredient concentration of 500 ppm, and the dilute solution was sprayed onto the plant at a rate of 15 ml/pot on a turn table. At the same time, the soil was drenched with 2 ml of the same dilute solution. After 8 days, the degree to damage of each plant by the mite was examined. The standard for judging the effect was as follows:

—: Little damage is observed.
+: Slight damage is observed.
++: Same damage as in the untreated plot is observed.

The results are shown in Table 10.

TABLE 10

| Test compound | Effect |
|---|---|
| (1) | — |
| (2) | — |
| (3) | — |
| (4) | — |
| (5) | — |
| (6) | — |
| (7) | — |
| (8) | — |
| (9) | — |
| (10) | — |
| (11) | — |
| (12) | — |
| (13) | + |
| (14) | — |
| (15) | — |
| (16) | — |
| (17) | — |
| (18) | — |
| (19) | — |
| (20) | — |
| (21) | + |
| (22) | — |
| (23) | — |
| (24) | + |
| (25) | — |
| (26) | + |
| (27) | + |
| (28) | + |
| (29) | — |
| (30) | — |
| (31) | + |
| (32) | — |
| (33) | — |
| (34) | + |
| (35) | — |
| (36) | — |
| (37) | — |
| (38) | + |
| (39) | + |

TABLE 10-continued

| Test compound | Effect |
| --- | --- |
| (40) | + |
| (41) | − |
| (42) | − |
| (43) | − |
| (44) | − |
| (45) | − |
| (46) | + |
| (47) | − |
| (48) | − |
| (49) | − |
| (50) | − |
| No treatment | ++ |

TEST EXAMPLE 5

INSECTICIDAL TEST ON COMMON MOSQUITO (*Culex pipiens pallens*)

The emulsifiable concentrate of each test compound prepared according to Formulation example 1 was diluted 200 times with water, and 0.7 ml of the dilute solution was added to 100 ml of ion-exchanged water (active ingredient concentration, 3.5 ppm). Twenty last instar larvae of common mosquito were freed into the water, and after one day, the mortality was examined.

The standard for judging the effect was as follows:
Mortality (%)
a: Not less than 90%
b: Not less than 10% to less than 90%
c: Less than 10%

The results ar shown in Table 11.

TABLE 11

| Test compound | Mortality (%) |
| --- | --- |
| (1) | a |
| (2) | a |
| (3) | a |
| (7) | a |
| (8) | a |
| (9) | a |
| (11) | a |
| (12) | a |
| (13) | a |
| (14) | a |
| (15) | a |
| (16) | a |

TABLE 11-continued

| Test compound | Mortality (%) |
| --- | --- |
| (18) | a |
| (26) | a |
| (27) | a |
| (31) | a |
| (32) | a |
| (35) | a |
| (36) | a |
| (37) | a |
| (39) | a |
| (41) | a |
| (42) | a |
| (45) | a |
| (46) | a |
| (47) | a |
| (48) | a |
| (49) | a |
| (A) | c |
| No treatment | c |

What is claimed is:

1. A compound represented by the formula (V):

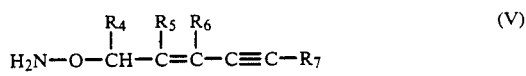

$$H_2N-O-CH-C=C-C\equiv C-R_7$$
with substituents $R_4$, $R_5$, $R_6$ on the respective carbons (V)

wherein each of $R_4$, $R_5$ and $R_6$, which may be the same or different, is hydrogen, $C_1$-$C_3$ alkyl, or optionally two of them bonded together to form a $C_2$-$C_4$ alkylene chain; and $R_7$ is hydrogen; $C_1$-$C_8$ alkyl; $C_1$-$C_8$ chloro- or fluoro-alkyl; $C_2$-$C_8$ alkoxyalkyl or $C_3$-$C_8$ cycloalkyl or phenyl which may be substituted with $C_1$-$C_3$ alkyl, $C_1$-$C_3$ alkoxy, a chlorine or fluorine.

2. A compound according to claim 1 wherein $R_4$, $R_5$ and $R_6$, which may be the same or different, are hydrogen or methyl.

3. A compound according to claim 1 wherein $R_4$, $R_5$ and $R_6$ are hydrogen.

4. A compound according to claim 1 wherein $R_4$, $R_5$ and $R_6$ are hydrogen; and $R_7$ is hydrogen; $C_1$-$C_8$ alkyl; $C_1$-$C_8$ chloro- or fluoro-alkyl; $C_2$-$C_8$ alkoxyalkyl or $C_3$-$C_8$ cycloalkyl which may be substituted with $C_1$-$C_3$ alkyl, $C_1$-$C_3$ alkoxy, chlorine or fluorine.

5. A compound according to claim 1 wherein $R_4$, $R_5$ and $R_6$ are hydrogen; and $R_7$ is hydrogen; $C_1$-$C_8$ alkyl; $C_2$-$C_8$ alkoxyalkyl; or $C_3$-$C_8$ cycloalkyl which may be substituted with $C_1$-$C_3$ alkyl, $C_1$-$C_3$ alkoxy, chlorine or fluorine.

* * * * *

UNITED STATES PATENT AND TRADEMARK OFFICE
CERTIFICATE OF CORRECTION

PATENT NO.   :   5,036,158
DATED        :   July 30, 1991
INVENTOR(S)  :   Naoto Meki, Kazue Nishida and Tomotoshi Imahase It is certified that error appears in the above-identified patent and that said Letters Patent is hereby corrected as shown below:

Title page, item [75] the inventors should be correctly indicated as
   follows:

[75]    Inventor:  Naoto Meki, Kobe, Japan; Kazue Nishida, Tokyo, Japan;
                   Tomotoshi Imahase, Kakogawa, Japan

[19]    should read --Meki et al--.

Signed and Sealed this

Second Day of March, 1993

Attest:

STEPHEN G. KUNIN

Attesting Officer        Acting Commissioner of Patents and Trademarks